US012496184B2

(12) United States Patent
Szente Varga

(10) Patent No.: US 12,496,184 B2
(45) **Date of Patent: *Dec. 16, 2025**

(54) STENT-GRAFT PROSTHESIS, SYSTEM AND METHOD FOR IMPROVED DELIVERY OF A STENT-GRAFT PROSTHESIS

(71) Applicant: Swiss Capital—Engineering AG, Zurich (CH)

(72) Inventor: Michael Szente Varga, Zumikon (CH)

(73) Assignee: Swiss Capital—Engineering AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,247

(22) Filed: Aug. 28, 2023

(65) Prior Publication Data

US 2023/0397980 A1 Dec. 14, 2023

Related U.S. Application Data

(63) Continuation of application No. 17/332,761, filed on May 27, 2021, now Pat. No. 11,779,453, which is a (Continued)

(30) Foreign Application Priority Data

Nov. 28, 2017 (EP) .................................... 17204247

(51) Int. Cl.
*A61F 2/07* (2013.01)
*A61F 2/852* (2013.01)
(Continued)

(52) U.S. Cl.
CPC ................ *A61F 2/07* (2013.01); *A61F 2/852* (2013.01); *A61F 2/856* (2013.01); (Continued)

(58) Field of Classification Search
CPC .. A61F 2/07; A61F 2/852; A61F 2/856; A61F 2002/061; A61F 2002/067; A61F 2210/0004; A61F 2250/0098
See application file for complete search history.

(56) References Cited

U.S. PATENT DOCUMENTS

| | | | |
|---|---|---|---|
| 2009/0048663 | A1 | 2/2009 | Greenberg |
| 2014/0180379 | A1 | 6/2014 | Fleming |
| 2018/0153677 | A1 | 6/2018 | Perkins et al. |

FOREIGN PATENT DOCUMENTS

| | | | |
|---|---|---|---|
| EP | 1847234 | A1 | 10/2007 |
| EP | 2606851 | A1 | 6/2013 |

OTHER PUBLICATIONS

WIPO, European International Search Authority, International Search Report and Written Opinion mailed Feb. 12, 2019 in International Patent Application No. PCT/EP2018/082912, 11 pages.

*Primary Examiner* — Dinah Baria
(74) *Attorney, Agent, or Firm* — Inskeep IP Group, Inc.

(57) ABSTRACT

The present application discloses a stent-graft prosthesis and a method for navigating such stent-graft prosthesis e.g. to a branch vessel. A first stent-graft prosthesis may include a main body and at least one lateral side branch connected to the main body. A further stent-graft prosthesis according to examples has a body having a generally tubular wall structure, the wall structure of the further stent-graft prosthesis including an orifice element (610) for receiving a guiding element (10). Preferably the wall structure has an overlap region (630) for interconnection, e.g. to the first stent-graft prosthesis. The orifice element (610) is then arranged at said overlap region, wherein said overlap region is preferably arranged at a proximal end region of said body. The guiding element (10) preferably is a textile thread or suture thread, optionally with a radiopaque marker, such as a fiducial
(Continued)

marker and/or a radiopaque elongate marker extending at least along a portion of a length of said guiding element (10).

8 Claims, 9 Drawing Sheets

Related U.S. Application Data continuation of application No. 16/767,565, filed as application No. PCT/EP2018/082912 on Nov. 28, 2018, now Pat. No. 11,045,303.

(51) Int. Cl.
*A61F 2/856* (2013.01)
*A61F 2/06* (2013.01)

(52) U.S. Cl.
CPC ... *A61F 2002/061* (2013.01); *A61F 2002/067* (2013.01); *A61F 2210/0004* (2013.01); *A61F 2240/001* (2013.01); *A61F 2250/0098* (2013.01)

STENT-GRAFT PROSTHESIS, SYSTEM AND METHOD FOR IMPROVED DELIVERY OF A STENT-GRAFT PROSTHESIS

RELATED APPLICATIONS

The present application is a continuation of and claims priority to U.S. patent application Ser. No. 17/332,761, filed May 27, 2021 entitled A Stent-Graft Prosthesis, System And Method For Improved Delivery Of A Stent-Graft Prosthesis; which is a continuation of and claims priority to U.S. patent application Ser. No. 16/767,565, filed May 27, 2020 entitled A Stent-Graft Prosthesis, System And Method For Improved Delivery Of A Stent-Graft Prosthesis (now U.S. Pat. No. 11,045,303 issued Jun. 29, 2021); which is a U.S. National Phase of and claims priority to International Patent Application PCT/EP2018/082912, International Filing Date Nov. 28, 2018, entitled A Stent-Graft Prosthesis, System And Method For Improved Delivery Of A Stent-Graft Prosthesis; which claims priority to European Application No. EP17204247.5 filed Nov. 28, 2017 entitled A Stent-Graft Prosthesis, System And Method For Improved Delivery Of A Stent-Graft Prosthesis, all of which are hereby incorporated herein by reference in their entireties.

FIELD OF THE INVENTION

This disclosure pertains in general to the field of tubular vascular prostheses. More particularly the disclosure relates to a vascular medical device being a covered stent, stent graft, endoluminal prosthesis or endoprosthesis for liquid communication with one or more side branch vessel(s), and a system of such devices, Also, medical procedures for deploying such devices and systems are disclosed. The target site in a patient includes for instance at least a portion of an aorta of a patient. More particularly, treatment of at least a portion of an aorta of a patient by implantation of such a device or system in a medical procedure is disclosed. The medical procedure is preferably minimally invasive vascular repair.

DESCRIPTION OF THE PRIOR ART

It is known to use modular covered stents or stent grafts for treatment or repair of vascular disease, such as e.g. an aneurysm. WO 2005/027784 discloses a system of modular covered stents for implantation in a diseased vessel, where the covered stents have apertures along the midsection of the covered stent. The apertures are used for aligning with branch vessels of a main vessel so that further stents can be connected at an aperture from a main vessel stent. The apertures need to be precisely aligned with the ostia of the side vessels. From the main vessel stent, a further stent graft protrudes then from each aperture into the branch vessel.

An undesired issue with such known devices is that it is difficult for the operator to correctly implant a stent-graft prosthesis in a main vessel aligned with branch vessels. Apertures or branches from the main vessel stent-graft prosthesis have to be correctly positioned in the main vessel in relation to the position of the branch vessels. The branch vessel is to be in liquid communication with the main vessel, i.e. through branch vessel stent-graft prostheses or portion of a larger stent graft unit with arms to the branch vessels.

In international patent application PCT/EP2017/062809 and EP 3 248 572 A1 (published after the priority date of this present application) of the same applicant as the present application, which are incorporated herein by reference in its entirety for all purposes, a stent-graft prosthesis and a method for navigating the stent-graft prosthesis to a branch vessel is disclosed. The stent-graft prosthesis includes a main body and at least one lateral side branch connected to the main body. A system of covered stents and a method for implanting, including interconnecting the stent-graft prostheses is also disclosed. Side vessel stent-graft prosthesis are disclosed in PCT/EP2017/062809 and EP 3 248 572 A1 which may be delivered to a side branch of a main stent-graft prosthesis through a special guiding catheter having a guiding mate threadable over a guiding element. The system is unique and innovative itself but may be further improved.

In EP 2 606 851 A1 a system is disclosed which includes an endoluminal prosthesis and a guide wire. However, navigation of side vessel stent grafts is difficult.

In the prior art, systems of covered stent modules are provided with stent-graft prostheses that have a varying diameter in e.g. a tapered shape. They are connected by inserting a first folded tapered shaped stent-graft prosthesis into a second expanded tapered shaped stent-graft prosthesis. When the first stent-graft prosthesis is expanded, the two stent-graft prostheses form a connection. Such a system causes an unnecessary additional task for the operator to keep track of in addition to keeping track of all the stent-graft prosthesis modules not only being in the right order, in the right direction before and during the entire operation but also need to keep track of where and how these two cones fit to each other. In contrary, examples of the present disclosure provide for a simpler, safer and quicker procedure of implantation.

There is a need for a further improved medical device and/or system, or medical procedures that are safer, avoiding the aforementioned drawbacks of known systems and procedures. Preferably a device and/or system or method is desired that makes the operation times shorter and delivery of the devices easier and more reliable to a lateral branch vessel. Procedures are desired to be more easily performed by the operator. Simplified implantation procedure is desired. Complication rate is desired to be reduced. Novel medical procedures with reduced patient risk are desired. Simpler implantation is desired. Medical procedures are desired, which can be performed despite the fact that they would be avoided today in a risk assessment of patients. For instance as known stent systems would have implied too high risk for complications and open chest surgery is no option for many patients, in particular elderly patients), such simplified implantation, or devices facilitating simplified implantation, are desired. Less X-ray dosage needed during the procedure is also desired. Hence, there is a desire to be able to provide novel medical procedures, implying reduced patient risk.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing medical devices, systems, and methods according to the appended independent patent claims.

The present novel stent-graft prosthesis system allows, amongst others, for individual, single delivery of side vessel stent branches. Examples of the invention described below allow advantageously reducing time for part of or an entire procedure. Implantation time is shortened compared to the prior art systems, and thus for instance the total dose is advantageously reduced. The angle of the x-ray modality needs to be changed less often than required by the prior art systems. Less amount of contrast medium is needed. Over all the below disclosure provides for reducing potential side effects for the patient. Moreover, the cost of the procedure will be reduced.

A reliable and stable delivery with precision positioning is provided while X-ray dosage is reduced as X-ray is not needed or substantially reduced to find the right overlap position for expansion of the prosthesis 600 at implantation.

The device and/or system may be used in medical procedures and methods as described herein.

Aspects of the disclosure include, but are not limited to, a stent-graft prosthesis.

In a broad sense, a stent-graft prosthesis is disclosed. It comprises a body having a generally tubular wall structure. The wall structure of the stent-graft prosthesis includes an orifice element for receiving a guiding element.

The stent-graft prosthesis may thus be delivered, preferably to a side branch of a main stent-graft prosthesis along a guiding element that is preferably at a distal end permanently or releasably attached at the side branch, preferably at an end portion of the side branch having the guiding elements distal end attached thereto.

A kit is disclosed including a first (main) stent prosthesis having a lateral branch and a second (side) stent-graft prosthesis according to such a broad sense. The first stent-graft prosthesis having at least one bendable and/or flexible guiding element being distally permanently or releasably attached to an interior of the at least one the branches at a distance from a distal orifice of the branch.

A system is disclosed including such a kit, wherein the guiding element is proximally extending through the orifice element for guiding the stent-graft prosthesis to the lateral branch towards the distal orifice of the branch during delivery, such that the orifice element is the stent-graft prosthesis upon delivery is arranged with a proximal overlap in the lateral branch.

A method of manufacture a stent-graft prosthesis is disclosed comprising providing a generally tubular wall structure of the prosthesis with an orifice element for receiving a guiding element.

A method of delivery a stent-graft prosthesis is disclosed, including in a vascular structure delivering a first stent-graft prosthesis having a side branch, the first stent-graft prosthesis having a guiding element distally permanently or releasably attached to an interior of the at least one the branches at a distance from a distal orifice of the branch, moving the second stent-graft prosthesis along the guiding element arranged through an orifice element of the second stent-graft prosthesis, and expanding the second stent-graft prosthesis with a proximal overlap in the side branch when the orifice element stops against a distal end of the guiding element.

The prosthesis 600 may include a body having a generally tubular wall structure. The wall structure preferably includes an orifice element 610 for receiving a guiding element 10. The orifice element is like a guiding mate in the prosthesis for receiving a guiding element 10 there through. The distal end of the guiding element 10 is arranged at a connection point 11 at a first prosthesis. Advancing the prosthesis 600 over the guiding element 10 arranged through the orifice element 610 until it distally stops, provides a defined distal position of the prosthesis 10 during delivery and implantation in relation to the first prosthesis.

The wall structure may have an overlap region for interconnection to another stent-graft prosthesis. The orifice element is then preferably arranged at the overlap region. The overlap region is preferably arranged at a proximal end region of the prosthesis body.

The guiding element 10 is elongate and suitable to extend through blood vessels and to be distally attached or connected to the body.

Preferably the guiding element 10 it is a textile thread or suture thread, optionally with a radiopaque marker, such as a fiducial marker and/or a radiopaque elongate marker extending at least along a portion of a length of the guiding element 10.

The guiding element 10 may alternatively be a (stiffer) elongate element like a wire. A wire has the advantage that it avoids buildup of a knot or muddle of the guiding element when a prosthesis (and/or catheter) is threaded along it.

The orifice element may be an aperture in the tubular wall structure. The aperture is preferably an eyelet in a wall material of the wall and preferably has a reinforced periphery edge or a reinforced peripheral region such as in the wall material adjacent the eyelet. The reinforcement may be provided by a suitable wire geometry of the stent structure of the prosthesis. For instance a heat set wire or laser cut structure may have an eyelet around the aperture/hole of the orifice element 610 in the wall structure of the prosthesis.

The orifice element may be a side opening or aperture in the wall structure.

The tubular wall structure has an outside. The orifice element may in examples be arranged at the outside of the wall. The orifice element may be an eyelet or a tubular element for receiving the guiding element 10.

The tubular wall structure has an inside. The orifice element may in examples be arranged at the inside of the wall. For instance the orifice element may include an elongate such as tubular structure for receiving the guiding element 10. The elongate structure may be arranged at the inside of the wall proximally and oriented towards an aperture in the wall. The guiding element 10 may then be arranged through the aperture and the tubular structure.

Alternatively or in addition to tubular structure(s) outside and/or inside the tubular wall structure, multiple eyelet structures may be provided at a suitable distance and along a suitable length to receive the guiding element through the eyelet structures along the length. The eyelet structures may be circular, oval or have other suitable cross sections.

The orifice element may be arranged at a rotational position of the tubular wall structure for facilitating a rotational position of the body upon delivery.

The orifice element is in examples a guiding mate. The guiding mate is configured for receiving the guiding element, such that the stent-graft prosthesis is configured to slide along the guiding element 10 during delivery over the guiding mate 9 to the orifice of the first stent-graft to be connected to the second stent-graft, such as of the branch.

Delivery and deployment of the stent-graft prosthesis is done through a delivery lumen of a catheter. The guiding mate for receiving the guiding element preferably has a distal end positioned proximally at a distance from the distal orifice at a connection point, such as of the side branch. In this manner the stent-graft prosthesis preferably extends distally beyond the connection point when the guiding mate 9 engages the connection point.

The guiding element 10 is preferably made of a biodegradable material.

Aspects of the disclosure include, a kit of a first stent prosthesis having a lateral branch and a second stent-graft prosthesis according to the above aspect.

The first stent-graft prosthesis may have at least one bendable and/or flexible guiding element 10 being distally permanently or releasably attached to an interior of the first stent-graft prosthesis at a distance from an orifice thereof. The guiding element 10 may be distally permanently or releasably attached to at least at one of the branches and at a distance from a distal orifice of the branch.

Aspects of the disclosure include, a system including the kit of the afore aspect. The guiding element 10 is preferably proximally extending through the orifice element for guiding the stent-graft prosthesis to a lateral branch 3 towards the distal orifice of the branch 3 during delivery. In this manner, the stent-graft prosthesis is upon delivery arranged with a proximal overlap in the lateral branch.

Aspects of the disclosure include, a method of manufacture a stent-graft prosthesis. The method may include providing a generally tubular wall structure of the prosthesis with an orifice element for receiving a guiding element 10.

Aspects of the disclosure include, a method of delivery a stent-graft prosthesis. The method may include delivering a first stent-graft prosthesis having a side branch 3 in a vascular structure. The first stent-graft prosthesis having a guiding element distally permanently or releasably attached to an interior of the at least one the branches (3) at a distance from a distal orifice of the branch 3. During delivery, the second stent-graft prosthesis is moved along the guiding element arranged through an orifice element of the second stent-graft prosthesis. The second stent-graft prosthesis is thus expanded with a proximal overlap in the side branch 3 when the orifice element stops against a distal end of the guiding element 10.

The guiding element 10 may provide securing of two prosthesis together. Upon expansion of the prosthesis 600 in the first prosthesis, a locking element may be threaded onto the distal end of the guiding element 10. The locking element may be a ratchet type locking element. The locking element may be a knot. The knot may be advanced along the guiding element 10 by means of a known knot-pusher device. The portion of the guiding element 10 proximal of the positioned and locked locking element may be cut/removed out of the body.

The stent-graft prostheses discussed herein are in an example self-expanding, or in another example expandable by another device, such as an inflatable balloon.

Further examples of the disclosure are defined in the dependent claims, wherein features for the second and subsequent aspects of the disclosure are as for the first aspect mutatis mutandis.

Some examples of the disclosure provide for an improved navigation of and assembling of a stent-graft prosthesis or a plurality of stent-graft prostheses. The stents to be assembled are to provide fluid communication upon delivery and assembly. For instance, a stent-graft prosthesis may be advantageously positioned in a side branch vessel from a main vessel. Fluid communication may be provided from a first stent-graft prosthesis in the main vessel to a second stent-graft prosthesis in such side vessel. Fluid communication may also be provided in other configurations requiring overlapping assembly of a plurality of modular stent-graft prostheses.

The term covered stent or stent-graft prosthesis means a stent or stent-graft having an inner and/or outer liner, shell or being otherwise surrounded by or provided with a liquid impermeable fabric or material. The covered stent can be partly or fully covered. A covered stent can also be called a stent graft or an endoprosthesis. Generally these stent-graft prostheses are tubular prostheses. The tubular prosthesis such as stents, grafts, and stent-grafts (e.g., stents having an inner and/or outer covering comprising graft material and which may be referred to as covered stents or stent-graft prosthesis) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded, porous polytetrafluoroethylene (ePTFE)) supported by a framework (e.g., one or more stent or stent-like structures), to treat or isolate aneurysms. The framework provides mechanical support and the graft material or liner provides a blood barrier.

A side branch 3 may be laterally extendable and/or collapsible, i.e. expandable in a direction of a longitudinal axis along the side branch 3, which direction is preferably substantially perpendicular to a longitudinal axis along a main body 2 of a stent-graft prosthesis 1. Alternatively, or in addition, the side branch 3 may be expandable in a transverse direction, i.e. expandable transverse to the direction of an axis along the side branch 3. The side branch 3 may comprise a stent-graft prosthesis and may in some examples be a covered stent.

In examples, the side branch 3 is about 1 cm to 1.5 cm laterally extendable.

The side branch 3 is in an example integral with the main body 2, either by the stent-graft prosthesis of the main body 2 and the stent-graft prosthesis of the side branch 3 being integral, or by the cover of the main body 2 and the cover of the side branch 3 being integral. In an example both cover and stent-graft prosthesis of the main body 2 is integral with the cover and stent-graft prosthesis of the side branch 3. When the side branch 3 comprises the stent-graft prosthesis it is stiffer and can then resist more handling when e.g. deploying and/or re-deploying any further covered extension stent-graft prosthesis. This also allows for the side branch 3 to form a tighter connection with any further covered extension stent-graft prosthesis out from the side branch 3.

Additionally, this allows for using a stent-graft prosthesis or a plurality of stent-graft prostheses in a system and assembly at the implantation target site, i.e. not pre-manufactured for a specific patient. This is an advantage over known systems. Known systems included hitherto pre-built, patient specific endoprosthesis. Usually, an image modality is used to scan the vessel system including the target site, e.g. a weakened aorta, earlier in time. The endoprosthesis is then manufactured based on the imaging data and delivered to the surgeon for implantation. This manufacturing of a patient specific endoprosthesis usually takes days to weeks, which is undesired. The anatomy of the vessel may change during this waiting time. The consequence may be that the manufactured endoprosthesis does not fit the patient anymore. Also, the waiting time is undesired as the patient mostly is in immediate need of the endoprosthesis, e.g. to avoid rupture of an aortic aneurysm. If desired, however, specific embodiments of the stent-graft prostheses of the present disclosure may be manufactured patient specifically. A standard setup of different sizes readily available for implantation is preferred, though, as waiting time due to manufacturing is avoided.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EMBODIMENTS

Figure 1:
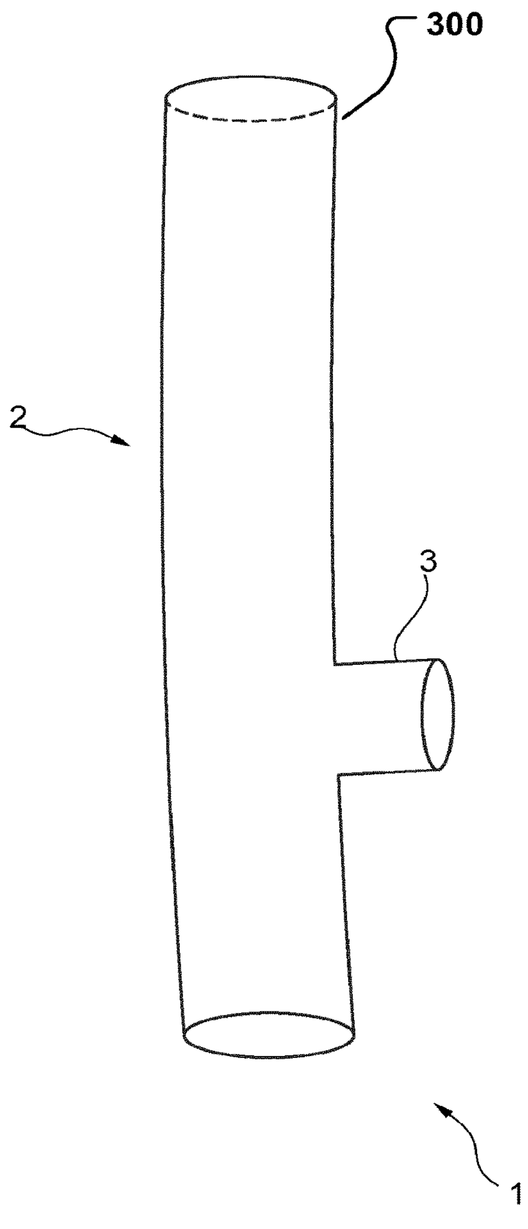
FIG. 1 is a schematic illustration of a stent-graft prosthesis with a side branch.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a medical device and in particular to a medical device for facilitating navigation of and assembling of a stent-graft prosthesis or a plurality of stent-graft prostheses in communication with at least a side branch vessel. The implant can be used for treatment and/or repair of vascular disease, such as e.g. aneurysm. The example is illustrated with an arrangement in the aorta. The vessel like the aorta may be structurally damaged of different reasons and need repair along at least a portion of the aorta 500. Sometimes extensive endoprosthesis are needed for aortic repair, partly or all the way from the ascending aorta 501 via the aortic arch 502 down the descending aorta 503 and along the abdominal aorta 504 past the renal arteries 505.

Figure 2:
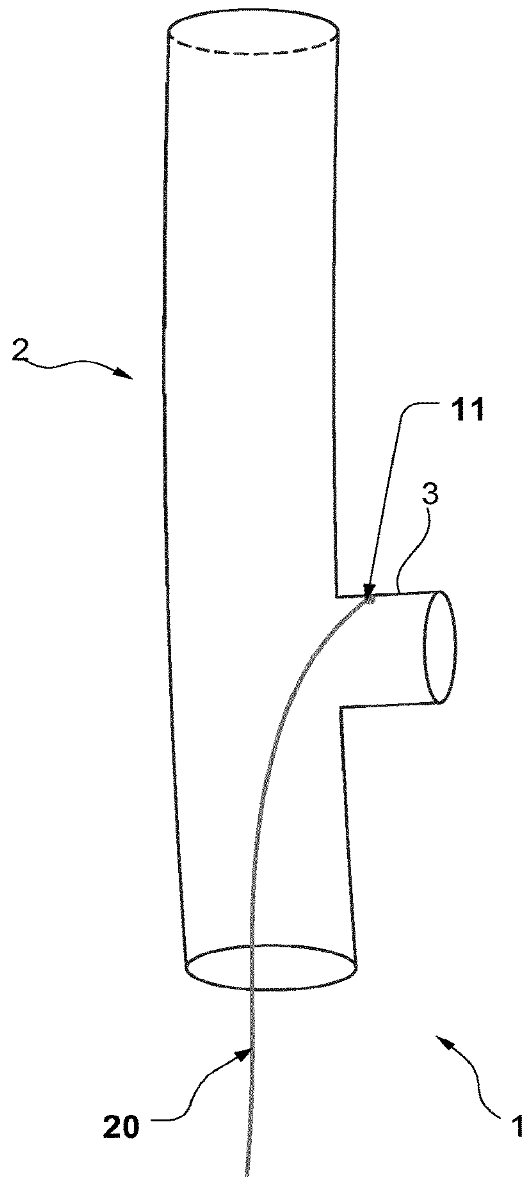
FIG. 2 is a schematic illustration of a stent-graft prosthesis with a side branch and a guiding element.

FIG. 1 is a schematic illustration of a stent-graft prosthesis 1 with a side branch 3. FIG. 2 is a schematic illustration of a stent-graft prosthesis with a side branch 3 and a guiding element 10.

Figure 3:
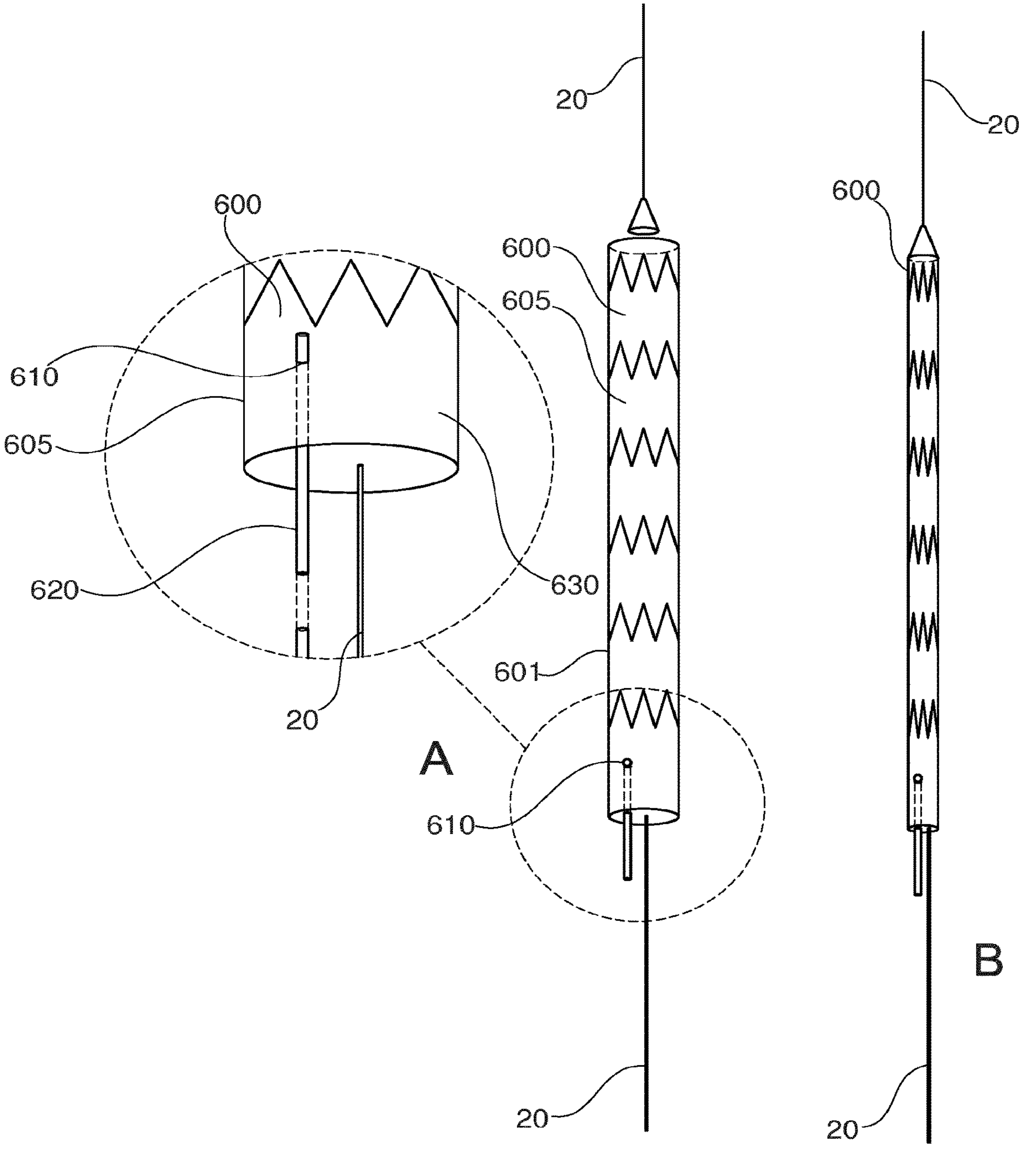
FIG. 3 is a schematic illustration of a stent-graft prosthesis with a guidewire arranged therein and an example of an orifice element for a guiding element.
Figure 4:
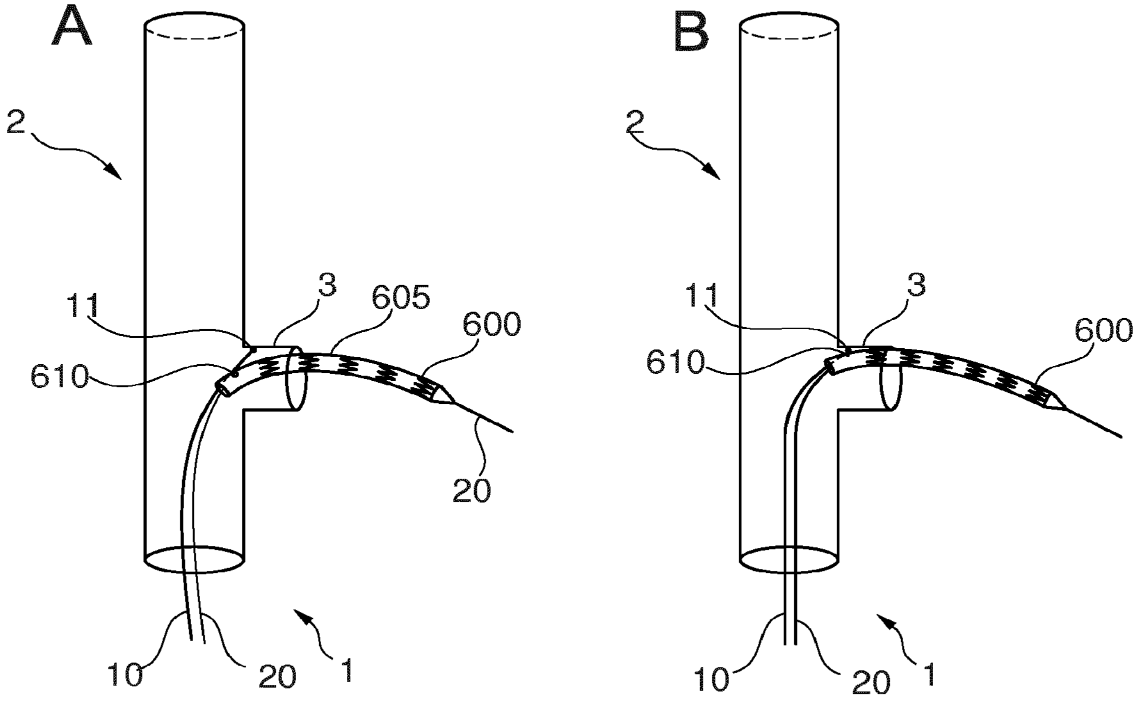
FIG. 4 is a schematic illustration of a stent-graft prosthesis partly delivered in an overlapping manner before expansion and fixation.
Figure 5:
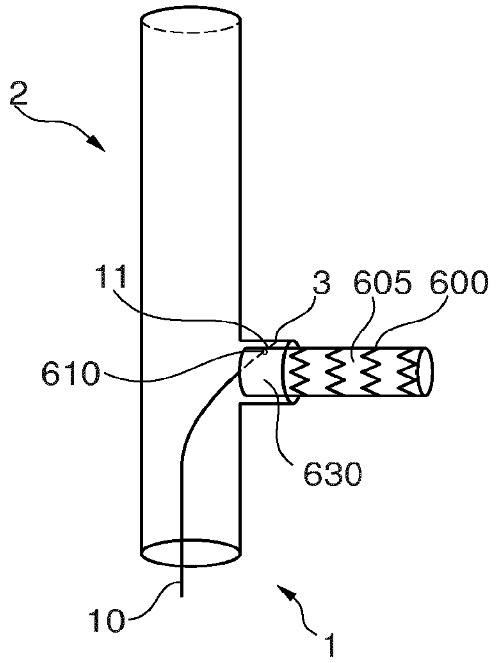
FIG. 5 is a schematic illustration of a stent-graft prosthesis delivered in an overlapping manner.
Figure 7:
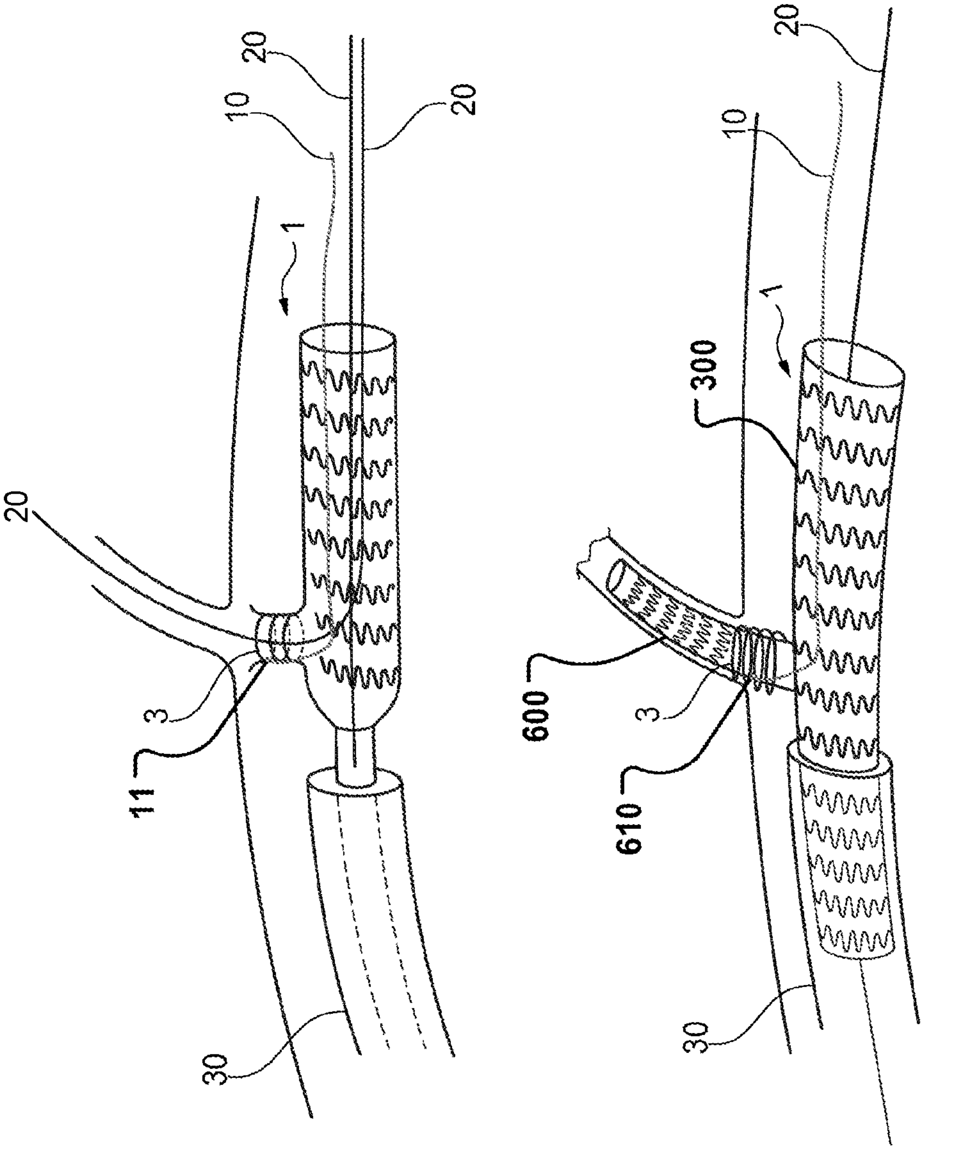
FIG. 7 is a schematic illustration of a stent-graft prosthesis before and after the stent-graft prosthesis is fully expanded.

FIG. 3 is a schematic illustration of a stent-graft prosthesis 600 with a guidewire arranged therein and an example of an orifice element 610 for a guiding element 10. The distal end portion is enlarged in part A of FIG. 3. Part B of FIG. 3 shows the prosthesis 600 collapsed (catheter and/or restraining member not shown) with the guiding element 10 easily insertable through a orifice element 610, here in an example including a tube 620. FIG. 4 is a schematic illustration of the stent-graft prosthesis 600 partly delivered in an overlapping manner before expansion and fixation. FIG. 5 is a schematic illustration of the stent-graft prosthesis 600 delivered in an overlapping manner. FIG. 7 is a similar schematic illustration of a stent-graft prosthesis 600 before and after the stent-graft prosthesis 600 is fully expanded;

The prosthesis 600 may include a body having a generally tubular wall structure 605. The wall structure 605 preferably includes an orifice element 610 for receiving a guiding element 10.

The prosthesis 600, in particular its wall structure, may have an overlap region 630 for interconnection to another stent-graft prosthesis. The orifice element 610 is then preferably arranged at the overlap region 630. The overlap region 630 is preferably arranged at a proximal end region of the prosthesis body.

The guiding element 10 is elongate and suitable to extend through blood vessels and to be distally attached or connected to the body. Preferably it is a textile thread or suture thread, optionally with a radiopaque marker, such as a fiducial marker and/or a radiopaque elongate marker extending at least along a portion of a length of the guiding element 10.

The orifice element 610 may be an aperture in the tubular wall structure. The aperture is preferably an eyelet in a wall material of the wall and preferably has a reinforced periphery edge or a reinforced peripheral region such as in the wall material adjacent the eyelet. The orifice element 610 may be a side opening or aperture in the wall structure, such as shown in the Figures.

The tubular wall structure has an outside. The orifice element 610 may in examples be arranged at the outside of the wall. The orifice element 610 may be an eyelet or a tubular element for receiving the guiding element 10 at the outside of the wall. It may be arranged at the outside only, such that it does not comprise a through going hole or aperture in the wall structure.

The tubular wall structure has an inside. The orifice element 610 may in examples be arranged at the inside of the wall. For instance the orifice element 610 may include an elongate such as tubular structure 620 (example in FIG. 3) for receiving the guiding element 10. The elongate structure may be arranged at the inside of the wall proximally and oriented towards an aperture in the wall. The guiding element 10 may then be arranged through the aperture and the tubular structure. It may additionally include an orifice element at the outside of the wall structure for guiding the guiding element 10, like an eyelet or open sock type element.

Alternatively or in addition to tubular structure(s) outside and/or inside the tubular wall structure, multiple eyelet, flap, skirt, fold or open sock type structures for receiving a guiding element 10 there through like a guiding mate. Multiple orifice elements may be provided at a suitable distance from each other and along a suitable length to receive the guiding element through the eyelet structures along the length. The eyelet, flap or open sock structures may be circular, oval or have other suitable cross sections.

The tubular structure 620, like a tube or catheter of desired length may be pre-arranged in a collapsed prosthesis 600, e.g. collapsed and kept in that collapsed state in a removable restraining member (not shown). The tubular structure extending through the opening in the wall structure 605 allows to position the guiding element through the opening in an advantageous manner when the prosthesis is collapsed and to be entered (or being positioned in) a catheter. In case the prosthesis is already in a catheter for delivery, the tube 620 may extend proximally all the way through the catheter to its proximal end so that the guiding element 10 can be threaded through the tube from its distal end/opening. The tube is a place-maker for the guiding element 10 to be easily positioned through the orifice element 610. The tubular element 620 may be part of the orifice element 610. The tube may also be short, just extending out of the proximal orifice of the prosthesis 600, such as shown in FIG. 3 at A and B. The tube 620 is preferably removable upon expansion/implantation of the prosthesis 600 in position in and connected overlappingly to the first prosthesis 1. The orifice element 610 may be arranged at a rotational position of the tubular wall structure for facilitating a rotational position of the body upon delivery. Thus, when the prosthesis 600 is advanced over the guiding element 10 (and maybe additionally along a guidewire 20 extending further distally than the distal end of the guiding element 10 at the connection point 11). Guiding element 10 will at the connection point 11 provide a stop for further advancing the prosthesis 600. Thus a reliable position of the prosthesis is provided in relation to the other prosthesis having the guiding element distally attached thereto.

The orifice element 610 is arranged like a guiding mate in the prosthesis for receiving a guiding element 10 there through. The distal end of the guiding element 10 is arranged at a connection point 11 at a first prosthesis. Advancing the prosthesis 600 over the guiding element 10 arranged through the orifice element 610 until it distally stops, provides a defined distal position of the prosthesis 10 during delivery and implantation in relation to the first prosthesis. The orifice element 610 shown in the Figures is merely an example.

The orifice element 610 is in examples a guiding mate. The guiding mate is configured for receiving the guiding element, such that the stent-graft prosthesis is configured to slide along the guiding element 10 during delivery over the guiding mate 9 to the orifice of the first stent-graft to be connected to the second stent-graft, such as of the branch.

Figure 6:
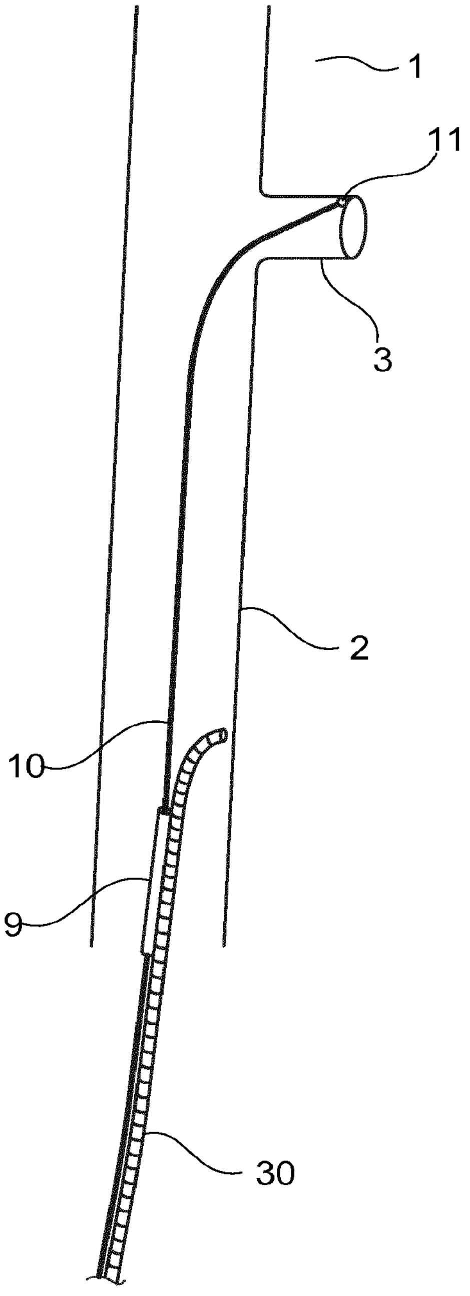
FIG. 6 is a schematic illustration of a stent-graft prosthesis with a side branch, and a catheter with a guiding mate for guiding the catheter for easy navigation of the side branch.

Delivery and deployment of the stent-graft prosthesis is done through a delivery lumen of a catheter. FIG. 6 is a schematic illustration of a stent-graft prosthesis with a side branch, and a catheter with a guiding mate for guiding the catheter for easy navigation of the side branch;

The guiding mate in form of an orifice element of a prosthesis is for receiving the guiding element. The guiding element preferably has a distal end positioned proximally at a distance from, preferably a distal, orifice of a first prosthesis at a connection point, such as of the side branch. In this manner the stent-graft prosthesis 600 preferably extends distally beyond the connection point when the orifice element 610 (guiding mate) engages the connection point.

The guiding element 10 is preferably made of a biodegradable material.

The guiding element 10 may alternatively even be non-biodegradable but biocompatible so that it safely can remain in the body (or be removed after use).

The guiding element 10 may alternatively to a suture or thread be a stiffer elongate element like a wire, e.g. of thermoplastic, metal or coated metal. A stiffer wire has the advantage that it avoids buildup of a knot or muddle of the guiding element when a prosthesis (and/or catheter) is threaded along it. A stiffer elongate element is preferably removable arranged from the body after use.

A guiding element 10 in form of a wire may be provided with similar or substantially identical flexibility properties as a guidewire 20 used to deliver the prosthesis 600. This is in particular advantageous as both the guidewire 20 and the wire 10 may be used to pull/push the prosthesis 600 along both wires during delivery.

A reliable and stable delivery with precision positioning is provided while X-ray dosage is reduced as X-ray is not needed or substantially reduced to find the right overlap position for expansion of the prosthesis 600 at implantation. Also, a wire generally has less risk to rupture during the delivery procedure.

A kit is provided in an example including a first stent prosthesis 1 preferably having a lateral branch and a second stent-graft prosthesis 600 described herein. The first stent prosthesis 1 has an orifice for overlappingly connecting second stent-graft prosthesis 600 to it.

It should be noted that the second stent prosthesis 600 may have further branches, possibly with own guiding elements for connecting further stent-graft prosthesis 600 to branches of it. Alternatively, or in addition, the stent-graft prosthesis 600 may have guiding element 10 at a connection point affixed to it for connecting stent-graft prosthesis 600. For instance the distal end of the stent-graft prosthesis 600 may comprise the connection point 11 while for instance a proximal end thereof includes the orifice element.

The first stent-graft prosthesis may in a more detailed example have at least one bendable and/or flexible guiding element 10 being distally permanently or releasably attached to an interior of the first stent-graft prosthesis at a distance from an orifice thereof. The guiding element 10 may be distally permanently or releasably attached to at least at one of the branches and at a distance from a distal orifice of the branch.

Aspects of the disclosure include, a system including the kit of the afore description. The guiding element 10 is preferably proximally extending through the orifice element 610 for guiding the stent-graft prosthesis to a lateral branch 3 towards the distal orifice of the branch 3 during delivery. In this manner, the stent-graft prosthesis is upon delivery arranged with a proximal overlap in the lateral branch.

Figure 12:
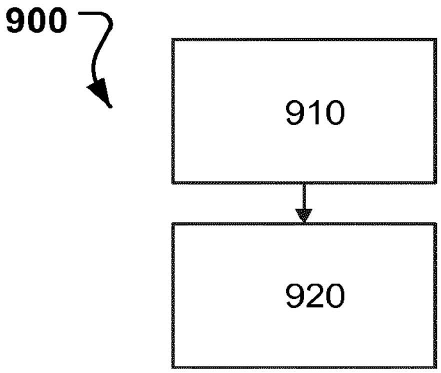
FIG. 12 is a flow chart of an example of a manufacturing method.

FIG. 12 is a flow chart of an example of a manufacturing method 900. The method 900 includes providing 910 a generally tubular wall structure of a prosthesis, and providing 920 the wall structure with an orifice element 610 for receiving a guiding element 10. Suitable methods for performing the steps will be known for the skilled person.

Aspects of the disclosure include, a method of delivery a stent-graft prosthesis. The method may include delivering a first stent-graft prosthesis having a side branch 3 in a vascular structure. The first stent-graft prosthesis having a guiding element distally permanently or releasably attached to an interior of the at least one the branches 3 at a distance from a distal orifice of the branch 3. During delivery, the second stent-graft prosthesis is moved along the guiding element arranged through an orifice element 610 of the second stent-graft prosthesis. The second stent-graft prosthesis is thus expanded with a proximal overlap in the side branch 3 when the orifice element 610 stops against a distal end of the guiding element 10.

The stent-graft prostheses discussed herein are in an example self-expanding, or in another example expandable by another device, such as an inflatable balloon.

Some examples of the disclosure provide for an improved navigation of and assembling of a stent-graft prosthesis or a plurality of stent-graft prostheses. The stents to be assembled are to provide fluid communication upon delivery and assembly. For instance, a stent-graft prosthesis may be advantageously positioned in a side branch vessel from a main vessel. Fluid communication may be provided from a first stent-graft prosthesis in the main vessel to a second stent-graft prosthesis in such side vessel. Fluid communication may also be provided in other configurations requiring overlapping assembly of a plurality of modular stent-graft prostheses.

By stent-graft prosthesis means a stent or stent-graft having an inner and/or outer liner, shell or being otherwise surrounded by or provided with a liquid impermeable fabric or material. The covered stent can be partly or fully covered. A covered stent can also be called a stent graft or an endoprosthesis. Generally these stent-graft prostheses are tubular prostheses. The tubular prosthesis such as stents, grafts, and stent-grafts (e.g., stents having an inner and/or outer covering comprising graft material and which may be referred to as stent-graft prostheses) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise bio-compatible graft material (e.g., Dacron® or expanded, porous polytetrafluoroethylene (ePTFE)) supported by a framework (e.g., one or more stent or stent-like structures), to treat or isolate aneurysms. The framework provides mechanical support and the graft material or liner provides a blood barrier.

A side branch 3 may be laterally extendable and/or collapsible, i.e. expandable in a direction of a longitudinal axis along the side branch 3, which direction is preferably substantially perpendicular to a longitudinal axis along a main body 2 of a stent-graft prosthesis 1. Alternatively, or in addition, the side branch 3 may be expandable in a transverse direction, i.e. expandable transverse to the direction of an axis along the side branch 3. The side branch 3 may comprise a stent-graft prosthesis and may in some examples be a stent-graft prosthesis.

In examples, the side branch 3 is about 1 cm to 1.5 cm laterally extendable.

The side branch 3 is in an example integral with the main body 2, either by the stent-graft prosthesis of the main body 2 and the stent-graft prosthesis of the side branch 3 being integral, or by the cover of the main body 2 and the cover of the side branch 3 being integral. In an example both cover and stent-graft prosthesis of the main body 2 is integral with the cover and stent-graft prosthesis of the side branch 3. When the side branch 3 comprises the stent-graft prosthesis it is stiffer and can then resist more handling when e.g. deploying and/or re-deploying any further covered extension stent-graft prosthesis. This also allows for the side branch 3 to form a tighter connection with any further covered extension stent-graft prosthesis out from the side branch 3.

In an example, the stent-graft prostheses have a substantially identical diameter at an inter-connection between two stent-graft prostheses to provide a liquid tight interconnection.

In an example, having the same diameter at an inter-connection means that the outer diameter at the inter-connection of one of the stent-graft prostheses is substantially the same as the inner diameter at the inter-connection of the other stent-graft prosthesis, at least along a portion of the stent-graft prosthesis. The same diameter is maintained at least along an overlapping portion of the two stent-graft prostheses, if overlapping. The two stent-graft prostheses are thus for instance liquid conveying connectable by overlapping each other and one tube inside the other connected tube.

The stent structure of stent-graft prostheses is part of the stent-graft prosthesis. It may have a pattern, like undulations. The pattern (such as schematically shown in e.g. FIGS. 3-5 and 7) may be made by made by braiding, weaving, laser cutting of a tube, etc. The structure is a scaffold to support the structure outwards and provide a substantially tubular structure to ensure undisturbed blood flow through the tube when implanted as it is provided with and covered by a suitable liquid tight cover.

The undulations or pattern can be denser at the overlapping connection region than other regions of the stent-graft prosthesis—for a secure liquid tight connection of two stent-graft prostheses and by improved mechanical strength.

In an example the two stent-graft prostheses to be inter-connected have both substantially the same inner diameter and substantially the same outer diameter at the interconnection, and the stent-graft prostheses are connected by overlapping them when one of the stent-graft prostheses is in a partially collapsed or folded state.

Having stent-graft prostheses with the same or substantially the same diameter makes it easy for the operator to connect the various stent-graft prostheses since the diameter of corresponding stent-graft prosthesis parts of the system 100 is similar and the operator does then not need to worry about any particular connection method, stent shape, connection site or the like. This means that the operator does only need to consider if the previous stent-graft prosthesis were a single, double, triple or further legged stent-graft prosthesis. This also makes the production of the stent-graft prostheses easier since the diameter at the connection of the various stent-graft prostheses are the same. An example is the diameter of legs 202, 203, stent-graft prosthesis 300 main body, and upstream oriented legs of the stent-graft prosthesis 400.

The overlapping region allows for length adaptation of the modular system. For instance the modular stent-graft prostheses, 400, 410, 420 could be provided as a single integral unit. However, providing straight middle piece stent-graft prosthesis 410 separate from branched end piece stent-graft prostheses 400, 420, allows for adjustment to specific patient anatomy (in the example different length of abdominal aorta). Overlap of the middle stent-graft prosthesis can be varied accordingly. Length adjustment of a system of modular stent-graft prostheses is provided by an overlapping portion at openings of stent-graft prostheses allowing for varying overlap and determining total length of the assembled modular system upon implantation. This applies, mutatis mutandis to side vessel extension stent-graft prostheses 600 connections, etc.

Providing the stent-graft prostheses 1 with substantially the same diameter gives the advantage that the operator can implant each stent-graft prosthesis 1 as explained above, or in an example in any direction he or she thinks is best. This will shorten the time required for assembling the system 100 and consequently the operation, drastically.

In an example, when the stent-graft prosthesis 1 has substantially the same diameter as discussed above and is expanded, or when a side branch 3 or leg of the stent-graft prosthesis 1 is expanded, a flow through the stent-graft prosthesis 1 is more or less unchanged through it. Meaning that a liquid, such as blood, entering at one side e.g. the main body 2 will pass through the stent-graft prosthesis 1 and out through e.g. two legs at the other side and due to the expansion and same diameter of connection at the stent-graft prostheses 1 an inlet and outlet area are substantially the same. This allows the operator to concentrate on connecting one stent-graft prosthesis 1 or part of a stent-graft prosthesis 1, such as a leg, at the time. The operator needs not to worry about the stent-graft prosthesis 1 disturbing the flow or throughput in the stent-graft prosthesis 1 or vessel. Use of orifice elements 610 and guiding elements 10 contributes likewise this advantage.

The modular stent-graft prosthesis system 100 further comprise one or more guiding element(s) 10, like a suture or wire. Along guiding element 10 a delivery catheter may be threaded proximally to the distal end of the guiding element 10. The guiding element 10 is distally affixed to a stent-graft prosthesis, for instance a suture may be affixed by means of a knot, staple, weld, adhesive, or similar. The guiding element 10 is thus secured to the stent-graft prosthesis. Preferably, the attachment point where the guiding element 10 is distally secured to the stent-graft prosthesis is at the interior, e.g. at a location of a lateral side branch of the stent-graft prosthesis. The guiding element 10 is preferably pre-loaded in a delivery catheter of the stent-graft prosthesis. The guiding element is in use operating as a guilder for a guiding mate 9 of a catheter. The guiding element 10 is preferably bendable and/or flexible.

In embodiments, the guiding element 10 is thus distally permanently or releasably attached to an interior of a branch, e.g. a lateral side branch, at a connection point, preferably at a distal orifice of the branch 3. The guiding element 10 is proximally arranged in the interior, through and along a proximal portion of the main body 2 or another of the branches 3 and extending proximally through a proximal opening of the main body 2 (see e.g. FIG. 3 or 8). In use the guiding element is thus operating for guiding a catheter over the guiding element 10 through the main body 3 towards the distal orifice of the lateral side branch 3.

See FIGS. 2 to 8 and the corresponding text herein for more detailed described examples of the guiding element 10 and its corresponding use and application in a modular stent graft system.

Alternatively, or in addition, a guiding element 10 can be distally attached to a vessel wall or an organ at a target location. It may for instance be attached to the wall of the aorta of a patient at a desired target location for a prosthesis having an orifice element for delivery. Delivery is performed in a similar manner as to a first stent-graft prosthesis having a connection point 11 with the difference that the connection point 11 is at the anatomical target location. The distal end of the guiding element is thus configured to be anchored at a tissue location. Anchoring may be provided by suitable anchoring means or unit(s) like barbs, staples, knotted sutures, etc.

Alternatively, or in addition, the attachment of a guiding element at its distal end may be releasable, preferably releasable from outside the body activation, for removing the guiding element during the implantation procedure, as needed. A knot may be releasable, thermal detachment means may be provided for controlled detachment of the guiding element at the attachment point. Alternatively, or in addition, the guiding element may be configured to be cut off after use. Suitable tools may be used for the cutting off, e.g. a sheath with an interior secure cutter slid over and along the guiding element towards the attachment point, where the cutter is activated and the guiding element cut off. The guiding element may then be securely retracted out of the body, e.g. within the sheath having the cutter, or just proximally drawn out of the vasculature via the puncture site/introducer.

However, the guiding element 10 is in examples configured to be left in place upon concluded implantation procedure. The guiding element 10 can thus be left in place after use (guiding delivery and deployment of e.g. an extension stent graft) or removed. It may be made of a biodegradable material or bioabsorbable material. The guiding element 10 is in any case made of a biocompatible material, including absorbables such as polyglycolic acid, polylactic acid, Monocryl and polydioxanone as well as the non-absorbables nylon, polyester, PVDF and polypropylene, PTFE or Dacron. The guiding element 10 may be made of metallic material, such as Nitinol or stainless steel, or a suitable metal alloy, which might be advantageous from a durability advantage during implantation. This may be advantageous during delivery as described above and also when the guiding element is left in place after concluded implantation procedure of the modular stent-graft prosthesis system. The procedure can be shortened as the guiding element needs not necessarily to be detached or cut off at or close to the connection point. It may be cut of at is proximal end only, or not at all.

Along guiding element 10, alternatively or in addition to stent-graft prosthesis 600 having an orifice element, a delivery catheter 30 may be moved towards the distal end of the guiding element 10, e.g. by means of a guiding mate 9 on the catheter as described herein (FIG. 6). Delivery of another element, device or unit, can then take place through this delivery catheter to a desired site at the distal end of the guiding element 10. X-Ray guidance, probing, navigation tries etc. can advantageously be reduced or omitted.

In this manner, a catheter can be moved along the guiding element to or towards the distal end thereof without fluoroscopic guidance. In this manner, reliably, and speed of delivery is improved while radiation exposure can be reduced.

Such a delivery catheter 30 is provided for delivery of an extension stent graft 600. The catheter 30 has a delivery lumen with a distal orifice for delivery and deployment of the extension stent graft 600 at a target site of a lateral side branch 3 of a stent-graft prosthesis 1.

The catheter 30 further has a guiding mate 9 for receiving a guiding element 10 distally attached to a connection point at the branch 3. Therefore, the catheter 30 is configured to slide along the guiding element 10 over the guiding mate 9 to the orifice of the branch for deployment of the element, such as the extension stent graft 600 through the delivery lumen of the catheter.

The guiding mate 9 for receiving the guiding element has a distal end positioned proximally at a distance from the distal orifice of the delivery lumen. In this manner the delivery lumen extends beyond the connection point when the guiding mate 9 distal end engages the connection point.

As can be seen e.g. in FIG. 6, the distal end of the delivery catheter 30 may be pre-bent to advantageously enter into the side vessel from the branch orifice. In this manner the operation time is reduced, fluoroscopic load of the patient and clinical personnel reduced, and the implantation made more securely and reliable.

A guidewire may thus be deployed in a side branch 3 through the catheter 30. Catheter 30 may then be withdrawn, the guidewire left in place. Stent-graft prosthesis may then be advanced into the side branch (see FIG. 4 at A and B). Upon expansion (FIG. 5) the guidewire 20 is removed.

A modular stent graft system is provided including a stent-graft prosthesis 1 and a delivery catheter 30 with a guiding element 10 arrangeable or arranged through a guiding mate 9. In this manner a unit, such as an extension stent graft 600 is advantageously deliverable through the delivery catheter 30 to a target site at a branch 3.

In addition, the distal end of the guiding element 10 is for example arranged at a marker 21. Alternatively, or in addition, the guiding element 10 may be provided itself with a marker. Marker means fiducial marker that is visualizable by suitable imaging means for the surgeon performing the implantation procedure. The marker 21 is preferably arranged at a leg 4 of a stent-graft prosthesis for guiding delivery of another stent-graft prosthesis towards and/or through the distal orifice of such a leg 4, e.g. as described below, to a side branch vessel of a main vessel. The marker may be elongate and extend along at least a part of the length of the guiding element 10, e.g. as a radiopaque strand of a multi-strand wire/suture/thread, and/or one or more marker bands.

The illustrated modular stent-graft prosthesis system 100 includes a first main vessel stent-graft prosthesis 200, 420 with a first upstream inlet branched into at least two downstream outlet branches.

Further it includes a stent-graft prosthesis type 300, 310, 320 that has a main body, and at least one lateral side branch connected to the main body. The lateral side branch is preferably flexible and expandable. The stent-graft prosthesis is interconnectable to one of the downstream outlet branches and laterally connectable to a side stream vessel of the main vessel via the lateral side branch thereof. At least two stent-graft prostheses 300, 310, 320 are thus sequentially interconnectable to one of the downstream outlets of the main vessel stent-graft prosthesis 200. In this manner, blood conduits are provided arranged in parallel by the at least two stent-graft prostheses, one at a time assembled by the operator. The parallel blood conduits may be provided with one or more side branches each. Alternatively, or in addition, a blood conduit in form of a stent-graft prosthesis may be provided that has no lateral side branch, which then provides a straight blood flow path in parallel with e.g. a stent-graft prosthesis having one or more lateral side branches.

The modular stent-graft prosthesis system further includes a second type of main vessel stent-graft prosthesis 400, 430 with at least two upstream inlet branches collected in a downstream outlet. The inlet branches are interconnectable to a distal outlet of one of the two stent-graft prostheses, e.g. stent-graft prostheses type 300, 310, 320 as shown in FIGS. 9 and 10.

Figure 9:
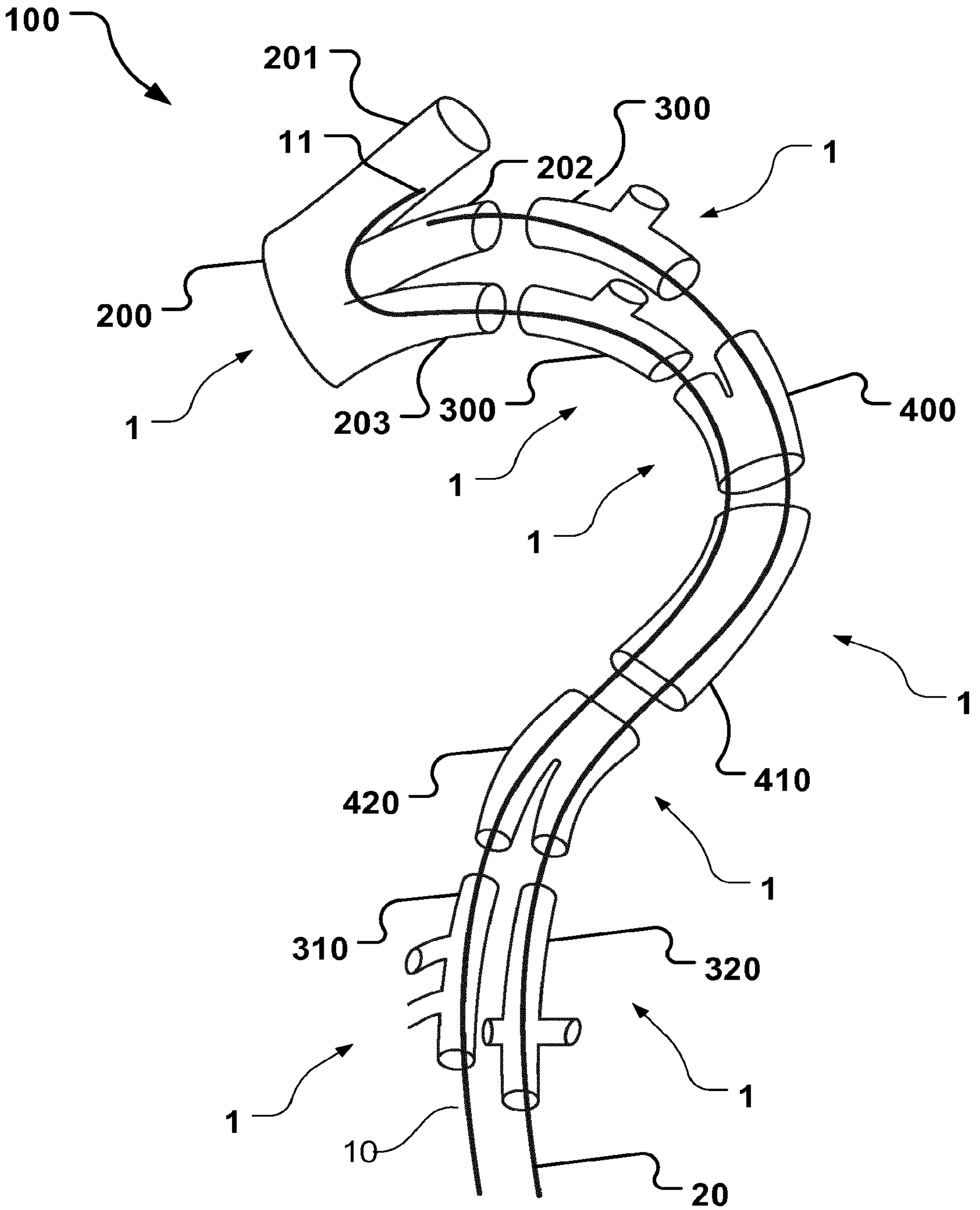
FIG. 9 is a schematic illustration that shows a system of different stent-graft prosthesis modules for implantation inside the aortic arch and thoracic aorta of a patient.
Figure 10:
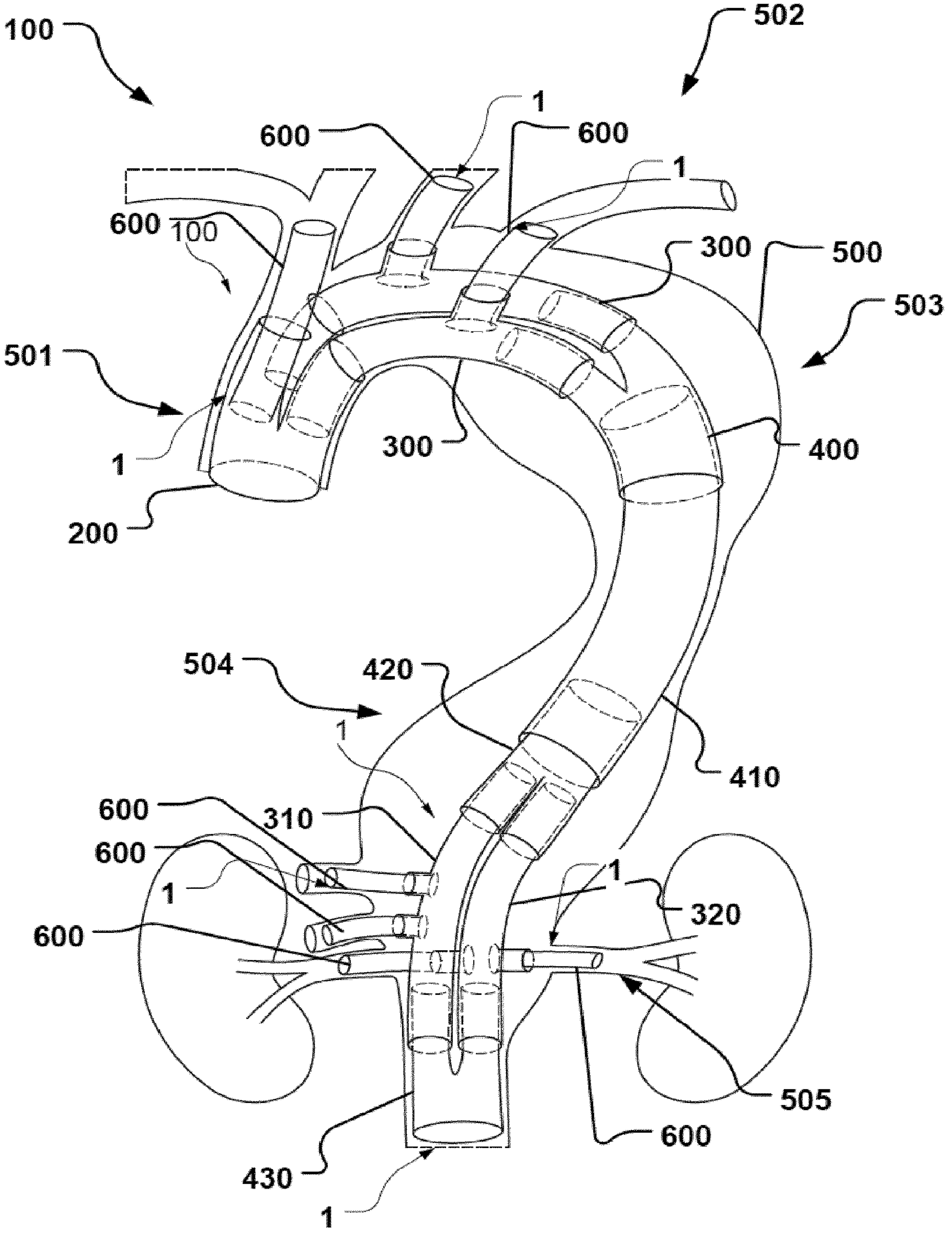
FIG. 10 is a schematic illustration that shows the system of FIG. 9 when it has been implanted inside the aorta of a patient.

Starting from the top of the system 100 as illustrated in FIGS. 9 and 10, there is illustrated a first stent-graft prosthesis 200 with three legs. This module is implanted firstly over a guidewire 20.

It should be noted that the stent-graft prosthesis modules are delivered in a specific order, starting with a three-legged stent-graft prosthesis 200 in the ascending aortic arch. Further stent-graft prosthesis modules are then delivered to the target site until the entire system is implanted. This is done in a very efficient and advantageous manner.

For instance, when the three legged stent-graft prosthesis 200 is deployed and implanted firstly of all modules in the ascending aortic arch. This can be done via a guide wire 20, e.g. in a femoral access approach. Further components can then be connected to the legs 201, 202, and/or 203.

For instance a stent-graft prosthesis 600 can be delivered to the first leg 201 via a delivery catheter slid along guiding element 10 to or towards connection point 11, such as in the manner described with reference to FIG. 1 to 5. This stent-graft prosthesis 600 can then extend blood flow e.g. into the first neck side vessel as shown in FIG. 10. The stent-graft prosthesis 600 is a stent-graft prosthesis without apertures for side vessels. The extension stent graft 600 is configured to be proximally matingly and fluid tight connected to the distal portion at the orifice of the first leg 201. Connection may be done overlappingly in a suitable manner and by suitable means known in the art of connecting stent grafts to each other for providing a communication channel for liquid there through to the target vessel.

Delivery is thus providable in two steps. Firstly, the side branch 3 is expanded. Then a side vessel stent-graft prosthesis 600 is deployed through the expanded side branch 3, preferably along a guiding element 10 and mating orifice element 610 for desired overlap. Fixation of the side vessel stent-graft prosthesis 600 is done then (FIG. 5 or 7). The entire prosthesis is flexible until the side branch is finally intubated, i.e. the side branch stent-graft prosthesis 600 is deployed and thus "locked" in position.

During delivery of stent-graft prosthesis 600, the two remaining legs 202, 203 are not obstructed and blood flow through the aortic arch is ensured during the implantation procedure, which is an important advantage.

The guiding element 10 is also running inside the third leg 203. This means, that over same guiding element 10 and delivery catheter over which the stent-graft prosthesis 600 was delivered, the stent-graft prosthesis 300 with a side branch is deliverable.

The initial guidewire 20 for delivering the three-legged stent-graft prosthesis 200 to its target site, is used for delivering and connecting a stent-graft prosthesis 300 to the second leg 202.

The location of three-legged stent-graft prosthesis 200 is preferably marked with a fiducial marker 21 that can be seen during imaging by e.g. MRI, CT or X-ray. Hence, shortened radiation times and dosages are providable.

As the guiding element 10 extends out from the first leg 201, all three legs can be located and modular stent-graft prostheses interconnected at the orifices of the three legs. No additional navigation, searching or probing by the surgeon is needed, thus reducing radiation times and dosages.

The guiding elements 10 are for guiding subsequent stent-graft prostheses along them so that the subsequent stent-graft prostheses can be connected to a previously implanted stent-graft prosthesis.

In addition, or alternatively a navigation element 20, such as a guide wire, is used instead for or together with one or more guiding element(s) 10 in the system 100 for guiding all or almost all of the stent-graft prostheses of the system 100 to their target site.

Next, the system 100 includes in proximal direction, downstream the aorta, two stent-graft prostheses 300 with one side branch each, positioned in the aortic arch 502 upon implantation. The two stent-graft prostheses 300 may include orifice elements 610 and are each guided by the guiding elements 10 and guidewire 20, respectively.

The side branch exit is preferably expandable, and in liquid communication with a neck vessel when expanded. A further stent-graft prosthesis 600 is further connected with its proximal end, respectively, extending into the remaining two neck vessels respectively (see FIG. 10). Delivery of these further stent-graft prostheses 600 can be done fiducial marker guided (not shown), with guidewires and contrast medium feedback, and/or a guiding element 10 can be connected to the branch (see FIGS. 1 to 5 and 7) facilitating delivery of the further stent-graft prostheses 600 through the orifice of the side branch of stent-graft prosthesis 300 and into the respectively neck vessel.

As the orifices of the lateral branches can be located at a distance from the ostia of a target site vessel thanks to the parallel arrangement of several stent-graft prostheses 300, the exact position in relation to each other (ostia/orifice) is not as important as for known stent-graft prostheses. Flexibility without risk for kinking is provided in particular with extension stent-graft prostheses 600.

Then, downstream the aorta there is proximally a stent-graft prosthesis 400 with two distal legs united into a single lumen body having a proximal orifice. The first leg of stent-graft prosthesis 400 is delivered running along guiding element 10 for interconnection with the proximal orifice of the stent-graft prosthesis 300, which in turn is previously distally interconnected to the third leg 203 of the distally and upstream in the aorta arranged and previously implanted stent-graft prostheses 300. The other distal leg of stent-graft prosthesis 400 is delivered along guidewire 20. It is distally interconnected to the proximal orifice of the other stent-graft prosthesis 300, which in turn is previously distally interconnected to the second leg 202 of the distally and upstream in the aorta. Thus the parallel stent-graft prostheses 300 are collected together in a single lumen.

A further stent-graft prosthesis 410, without side branches or legs is distally interconnected to the proximal orifice of stent-graft prosthesis 400. The further stent-graft prosthesis 410 is delivered over both the guiding element 10 and guidewire 20 which both are run inside this stent-graft prosthesis 410 through one of the distal legs of stent-graft prosthesis 400 respectively. In case the stent-graft prostheses 300 include one or more guiding element(s) 10, previously used for the extension stent-graft prostheses into the neck vessels, these one or more guiding element(s) 10 will also be run through the lumen of stent-graft prosthesis 410.

Overlap of stent-graft prostheses, such as 400, 410, 420, can be adapted during implantation to accommodate the patient aortic anatomy. Orifice element(s) 610 facilitate finding of a suitable overlap position before expansion/release of the stent-graft-prosthesis 600.

Next in downstream aorta direction is a two-legged stent-graft prosthesis 420 is implanted/provided and branching the blood flow into two proximal legs from a distal common lumen and orifice interconnectable to proximal orifice of the distal stent-graft prosthesis 410 previously implanted. Guiding element 10 runs inside the first leg. Guidewire 20 runs inside the other leg. The two legged stent is delivered over the two latter in a delivery catheter, which may be the same as used for delivery of previously distally delivered modules.

And finally, at the bottom of the drawing, two stent-graft prostheses 310, 320 are illustrated, with two side branches 3 each.

The first stent-graft prosthesis 310 is delivered by means of guiding element 10 (catheter slid over guiding element 8 to the leg of stent-graft prosthesis 420). A further delivery catheter may be used for this purpose, where the guiding element runs all the way through the first stent-graft prosthesis 310. One or more further guiding element(s) 10 may be attached to one or more of the side branches of the first stent-graft prosthesis 310 for delivery of extension stent-graft prostheses 600 extending into side vessels, see FIG. 10 when implanted.

The second stent-graft prosthesis 320 is delivered by means of guidewire 20. A delivery catheter is again used for this purpose, such as described above. A further guiding element 10 may be attached to one or more of the side branches of the second stent-graft prosthesis 320 for delivery of extension stent-graft prostheses 600 extending into side vessels, see FIG. 2 when implanted.

The proximal end of the two stent-graft prostheses 310, 320 are interconnected to two distal legs of a two legged stent-graft prosthesis 430 to provide a liquid path thereby. Guidewire 20 and guiding elements 10 run accordingly through stent-graft prosthesis 430.

As described above, the system 100 is thus positioned as shown in FIG. 10.

In an example a method of interconnecting a plurality of stent-graft prostheses is provided which can be performed either in vivo and/or in vitro.

In an example, before assembly, and/or during assembly, the stent-graft prostheses of the system 100 are sorted and placed in the correct order for assembly. In an example, and if assembled during implantation, a number of catheters 30 may be used as described and needed. The components of the system may be provided as a kit with suitable numbering to facilitate implantation for the surgeon. The kit components and composition may be computer plant prior to the implantation procedure. A software may be provided to support the surgeon and/or clinical personnel to perform the procedure. The surgeon may virtually plan the procedure in advance. Sequence of components, preferably with numbers in the kit components, and procedural steps may then be suggested by software during the implantation procedure. Quality assurance may be provided by entering into the software feedback of components used and steps performed. X-ray images and timestamps and other medical equipment measurement or input data may be saved too. The procedure may thus be efficiently performed and documented at the same time.

Although not shown in FIG. 1, further navigation elements 20 and/or guiding elements 10 may be provided for navigation of the side branches 3 and aligning of the side branches 3 with branch vessels, as explained. To make it easier to see which navigation element 20 or guiding element 10 that goes to a certain stent-graft prosthesis, leg or side branch, each navigation element and guiding element is labelled in an example.

Figure 8:
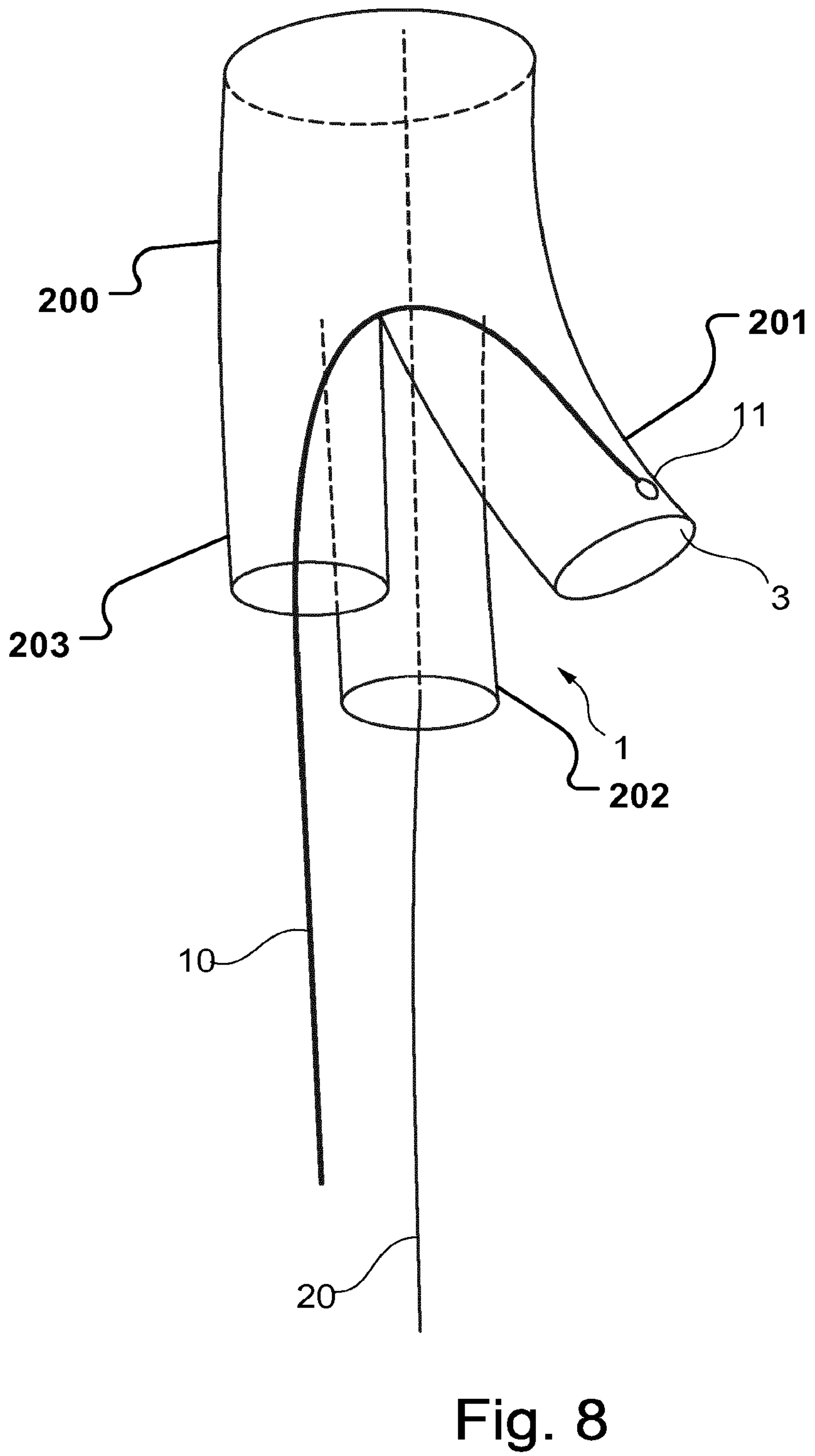
FIG. 8 is a schematic illustration of a stent-graft prosthesis with three legs, and a navigation element and a suture for easy navigation to all three legs.

FIG. 8 illustrates a stent-graft prosthesis 200 with three legs 201, 202, 203, and a navigation element 20 and guiding element 10 in from of a suture for easy navigation to all three legs. FIG. 8 illustrates an example of how one or more (one shown) guiding element 10, such as a suture, may run through a stent-graft prosthesis during implantation of a system 100 of stent-graft prostheses.

The three legs 201, 202, 203 are provided for connection to three aortic arch side vessels: one into the neck artery, and two through channels (when assembled) with side branch vessel connection. The three legs 201, 202, 203 may have different lumen diameter and length. The pre-attached guiding element 10 extending into one leg (203) and into another leg (201) allows for a direct intubation of a side vessel. Direct access is provided to all side branches of the prosthesis without the difficulty of locating the side branches with the open legs of such an implant. This has hitherto been difficult to navigate, due to the length of the delivery catheter where the operator usually has no feeling for targeting to a side vessel. Also the pulsating blood flow during the procedure, and other procedural difficulties of intubation of side branches, are less relevant than for known stent-graft prosthesis. 3D to 2D visualization difficulties are avoided, less x-ray dosage is needed, the procedure is provided with significant time reduction, and reduced patient risk.

FIG. 8 further illustrates that one or more guiding elements 10, such as sutures, may be attached to the stent-graft prosthesis 200. In the figure, the suture 10 is attached inside the second leg 4 and extends out through the third leg. The guiding elements 10 have, as discussed above, a similar purpose to the purpose of the navigation element 20 of guiding delivery catheters for delivery of stent-graft prostheses such that they can be connected to form the system of stent-graft prostheses 100.

The operator can easily locate the two legs and navigate further stent-graft prostheses to any of the two legs. The operator can via the guiding element 10 navigate a first further stent-graft prosthesis 600 to the leg 201 where the guiding element 10 is attached. When the first further stent-graft prosthesis 600 is correctly positioned and connected to the three-legged stent-graft prosthesis 200, the operator can, via the same guiding element 10, navigate a second further stent-graft prosthesis to the leg 203 where the suture exits proximally from the three legged stent-graft prosthesis 200. The navigation element 20 ensures that the operator can locate also the third leg, as shown in FIG. 8, and deliver units that way as desired.

In an example as illustrated in FIG. 8, the navigation element 20, here a guide wire, runs inside and through the three legged stent-graft prosthesis 200 via a leg 202. During implantation of the system 100, the navigation element 20 is inserted far enough into the vessel so that any stent-graft prosthesis can follow the navigation element 20 to a desired target site location.

In an example, the stent-graft prostheses are guided to their respective position by sliding them along a navigation element 20 inside a delivery catheter. Upon release out of the distal catheter end, the stent-graft prostheses are expanded into place and implanted at that target site. Restraining members 8 may be provided.

Overlap with stent-graft prostheses 1, 300, 600 may be chosen according to patient anatomy during the implantation procedure. The connection point 11 can be adjusted accordingly (to patient anatomy) when affixing the guiding element 10 distally prior to implanting the prosthesis with the connection point. Thus overlap is automatically adjusted to the specific patient. Normally, a suitable overlap (position of connection point 11 in relation to the orifice element position) will be based on average patient anatomies.

The guiding element 10 is used thus for guiding further stent-graft prostheses to a connection location so that the stent-graft prostheses can be connected together into to the system 100 of stent-graft prostheses.

Generally, one advantage of using the guiding element 10, such a suture, instead of or in addition to the navigation element 20, such as a guidewire, is that a suture or a wire is provided flexible and can be bent and manipulated as desired without breaking. The navigation element 20 when being a guidewire is in some examples stiffer such that it can exert a distal force from the operator for e.g. pushing along a vessel from a puncture site. A catheter is then thread over the guide wire and moved along the guide wire. The guide wire may then be removed from the catheter for delivery of a unit through the catheter.

The flexible characteristics of the guiding element 10 allows for e.g. the stent-graft prosthesis to be placed into positions and/or navigated around e.g. corners in the stent-graft prosthesis and/or in a vessel and/or side branch 3. The guiding element 10 runs in embodiments outside of a delivery catheter lumen through which a unit is deliverable. Alternatively, or in addition, a guiding element may run through the same lumen as the lumen for delivery of a unit.

Preferably the distal tip of the catheter 30 has a design such that the distal orifice extends beyond the attachment point of the distal end of the guiding element 10. This can for instance be provided by a longitudinal recess (not shown) in the catheter lumen wall into which the guiding element 10 fits. The distal end of the catheter 30 with its delivery orifice may then protrude beyond the attachment point 11 where the proximal end of the recess will be positioned when the delivery catheter 30 is pushed distally forward. The recess may be a longitudinal slit. The recess may have at least a V-shaped portion to allow the guiding element 10 to be caught or introduced more easily in the recess. The catheter 30 may be slightly wiggled and/or rotated to allow the guiding element 10 to enter the recess.

As explained previously in relation to guiding element 10, the position 11 where the distal end of the guiding element 10 is permanently or releasably attached to the stent-graft prosthesis is advantageously provided with a marker, so that it can easily be seen during scanning by e.g. MRI, CT or X-ray. The connection point 11 serves as a stop unit for guiding element 10 to prevent a tangible resistance and further distal advancement of catheter 30 by the surgeon during the delivery procedure.

FIGS. 1 and 2 illustrate a stent-graft prosthesis 1 with a side branch and is an example a stent-graft prosthesis 300 with a side branch 3 of the exemplary system 100 (FIGS. 9 and 10).

The stent-graft prosthesis 1 has a main body 2, which is a stent-graft prosthesis, and a lateral side branch 3 connected to the main body 2. The side branch 3 protrudes out from the main body 2 and is flexible and expandable. One advantage of the side branch 3 being flexible and expandable is that the side branch 3 is easily movable in at least one dimension independent of the movement of the main body 2 such that a branch vessel can be found and more easily aligned with during implantation to enter into with the side branch 3. Alternatively, or in addition, the stent-graft prosthesis 1 has a plurality of legs and wherein at least one of the legs comprises a side branch 3. Thus, in an example (not shown) the stent-graft prosthesis 1 has a plurality of legs and each leg comprises a side branch 3. In an example the side branch 3 is deflated, collapsed or folded and may look like the side branch 3 of FIG. 1. Collapsed may include radially and/or longitudinally collapsed states, allowing reduced cross-section for delivery.

The stent-graft prosthesis 1 or side branch 3 may include wires that are suitably arranged as a stent/supporting frame part of the stent-graft prosthesis. In an example the wires may have a U shape in a longitudinal direction of the stent-graft prosthesis. In another example the wires may be helically wound.

In an example the wires may be wires interwoven with the covering. The wires may form a mesh, like a knitted pattern or a braiding. The wires may also be laser cut to form the springy pattern of the stent part.

Alternatively, or in addition, the wires or other expansile components of the present device may be made of a shape memory material. The shape memory effect of such wires may provide for a change of shape, such as collapsed to expanded shape, by means of known triggers like temperature. Suitable materials include Nitinol, CrMo alloys, shape memory polymers, etc. Shapes of components of embodiments made of such materials may be provided by heat treatment. Components of embodiments of such materials may rely solely on elastic or superelastic properties (e.g. Nitinol) for a change of shape from a collapsed or compressed configuration to an expanded, released, configuration.

When the stent-graft prosthesis 1 is made in a resilient configuration, upon exiting a delivery catheter, it will resiliently expand out from the main body of the stent-graft prosthesis, as for instance described below with reference to FIG. 3-5 or 7.

Alternatively, or in addition, the orifice element 610 like guiding mate 9 comprises a ring, eyelet, snarl, or loop for threading through of the guiding element 10. An inner diameter of the orifice element 610 like guiding mate 9 is matched to receive an outer diameter of the guiding element 10 with some tolerance to avoid too much friction between the two elements for sliding motion along each other.

The orifice element 610 like guiding mate 9 is a unit for matingly receiving the guiding element 10 there through for being slidingly movable along the orifice element 610 like guiding mate 9 to and from the guiding mate's distal end where it is preferably attached to a stent-graft prosthesis. The guiding element 10 is configured to be threaded through the orifice element 610 like guiding mate 9 for being slidingly moveable along the guiding mate 9. Threading through of the guiding element 10 is suitably done outside of the patient at the proximal end of the guiding mate, e.g. a suture, thread, filament or wire, of e.g. multifilament strands, that are for instance braided together, to form a flexible guiding unit 10.

Alternatively, or in addition, the guiding mate 9 can be a lumen of a dual (or multi) lumen catheter or any other suitable element which is configured to allow sliding on the guiding element 10 and preferably does not damage the vessel or lumen it is used in.

For easier alignment with a branch vessel, the stent-graft prosthesis side branch 3 can be provided with a marker 21. The marker 21 will make it visible to the operator when the side branch 3 is level or aligned with a branch vessel. By having only one marker at the side branch 3 it will be easier for the operator to align the stent-graft prosthesis 1 to its desired location by use of an imaging device, such as X-ray, than today's stent-graft prostheses having a plurality of markers that need to be brought in alignment in fluoroscopy. The marker 21 is in examples any fiducial marker visible under common type if imaging devices used in healthcare or stent-graft prosthesis placement such as MRI, X-ray, Ultrasound, and so on. Stent-graft prosthesis structures usually are themselves difficult to see under e.g. fluoroscopy. Markers may e.g. made of gold or similar materials allowing good visibility in such imaging.

In an example, the side branch 3 is folded or collapsed and restrained by a guiding element 10, such as a suture 10. The guiding element 10 is for instance wrapped around the side branch 3, and is releasable connected on the inside of the side branch 3 or otherwise attached to the side branch 3 causing it to be releasably folded or collapsed. Pulling the guiding element proximally then releases the side branch 3 from the collapsed state to the expanded state. Guiding element 10 remains in place for use as a catheter guide and/or a prosthesis with an orifice element 610.

An Example of a Side Branch Prosthesis 300 Implementation can be as Follows:

- Length of prosthesis side branch 3 may be approx. 15 mm
- Some other exemplary but not limiting measures are given in FIG. 7
- The pre-load guiding element 10 feature:
  - It is secured with the side branch, preferably in a position that assists to manipulate the orientation of the catheter to matingly engage the guiding element 10. The connection point is e.g. at the distally oriented inner side of the branch 3 such that the guide catheter 30 can be advantageously navigated through the lumen of the branch 3 towards a side vessel orifice or lumen.
  - The pre-load guiding element 10 works as a guilder for a catheter 30, e.g. the double lumen catheter shown in FIG. 6 to reach the side vessel.
  - The pre-load guiding element 10 is preferably configured to unlock from the prosthesis easily.

An Example of a Visceral Side Branch 310 can be as Follows:

- The prosthesis side branch 3 can be provided to maintain a certain angel in relation to the main body 2 longitudinal axis, e.g. approximately a 30-degree angle or a 45-degree angle to assist a surgeon to enter a side vessel with the catheter 30.
- The inner diameter of a side branch may be in the range of about 7 mm,
- The side branch prosthesis 3 is provided to allow a certain level of movement to allow adjustment to various connection angles towards side vessels.

Figure 11:
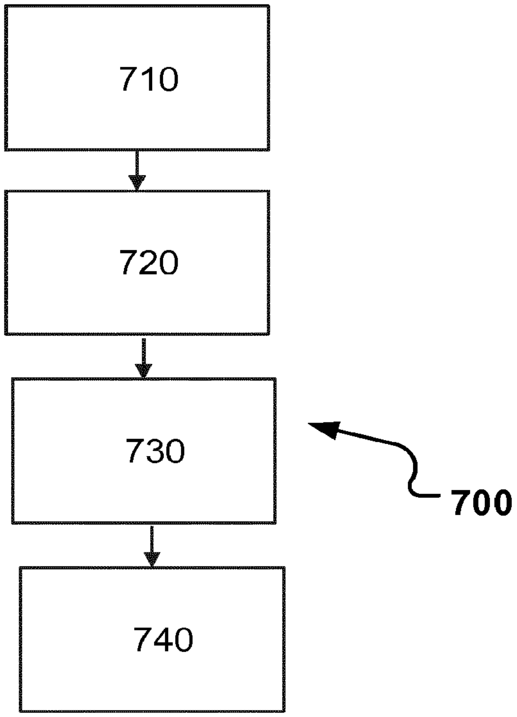
FIG. 11 is a flow chart of an example of a medical procedure.
Figure 11:
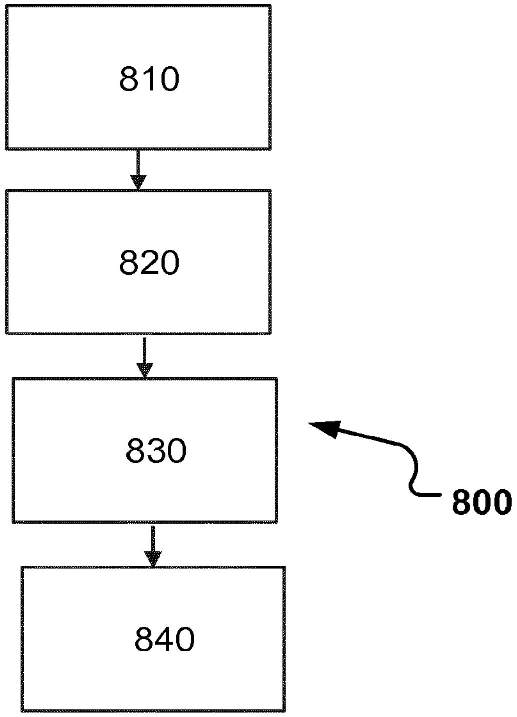

FIG. 11 shows flow chart examples of a medical procedure.

The method 700 comprises the steps of accessing 710*a* target site being a vessel in a patient; delivering 720 a first stent-graft prosthesis to the inside of the vessel at the target site through a delivery catheter, wherein the target site has a side branch vessel; delivering 730 a second stent-graft prosthesis to the first stent-graft prosthesis; connecting 740 the first stent-graft prosthesis to the second stent-graft prosthesis for providing a blood flow to the side branch vessel. The delivery of the second stent-graft prosthesis includes sliding a catheter 30 along a guiding element 10 to a position inside a lumen of a side branch of the first stent-graft prosthesis; delivering a guidewire to the side branch, removing the catheter 30, delivering and expanding the second stent-graft prosthesis along guiding element 10 and along orifice element 610 for connecting to the first stent-graft prosthesis. The catheter 30 with guiding mate 9 are thus in the method used for the delivering of a guide wire. Once the guidewire is in place in the side branch and extends sufficiently long into the side vessel at the side branch, the catheter 30 may be retracted. A covered extension stent 600 can then be delivered over that guidewire to the side vessel, see e.g. FIG. 3-5 or 7.

Alternatively, or in addition, the method 800 is provided. The second stent-graft prosthesis may have a side branch 3. The method includes delivering a second stent-graft prosthesis to a side vessel through a side branch 3 of the first stent-graft prosthesis. The method 800 comprises the steps of accessing 810 a target site being a vessel in a patient; delivering 820 a first stent-graft prosthesis to the inside of the vessel at the target site through a delivery catheter, wherein the target site has a side branch vessel; expanding 830 the side branch 3, delivering 840 a second stent-graft prosthesis to the first stent-graft prosthesis, preferably along a guiding element 10 attached distally to the first stent-graft prosthesis arranged through a orifice element 610 of the second stent-graft prosthesis, and through the side branch 3 to the side vessel; connecting 850 the first stent-graft prosthesis to the second stent-graft prosthesis for providing a blood flow to the side branch vessel. A catheter 30 with a guiding element 10 can be used between steps 830-840 as described above.

In a specific example the method includes delivering and assembling the system 100 as explained above and with a final layout illustrated in FIGS. 9 and 10 The example of such an endoprosthesis including modular embodiments and assembly is illustrated in FIGS. 9 and 10 and the corresponding text herein. Total aortic reconstruction or repair can be provided when implanting the entire system as shown in FIG. 10. Reference is made to FIGS. 1 and 2 and the corresponding text in international patent application PCT/EP2017/062809 of the same applicant as the present application, which is incorporated herein by reference for all purposes. Partial aortic reconstruction or repair may be provided with selected sub-modules of the system being implanted only. However, other anatomical structures may be provided for treatment with the devices and/or systems of the disclosure, including abdominal stent-graft prostheses, peripheral stent grafts, endoluminal prosthesis, and include e.g. but not limited to peripheral veins, leg arteries, spinal vessels, neuro structures, lymphatic system, etc.

The method starts in the example with soft guidewire being inserted into a vessel of a patient. Using a soft guidewire ensures that no part of the vessel is damaged during insertion. Further, the soft guidewire can be bent and thereby be navigated through the vessel system of the patient to a target site, here in the example the ascending aorta. As explained above other target sites in the body could also be chosen as an alternative.

Then, a first catheter is inserted, over the soft guidewire, into the vessel of the patient and navigated until it reaches the target site. Guided by the first catheter, a stiffer navigation element 20 is then inserted into the catheter and thus vessel of the patient.

The target site in the example is the ascending aorta where the three legged stent-graft prosthesis 200 is then positioned via the delivery catheter in the aortic arch. The delivered state, assembled with further components in the aortic arch is illustrated in FIG. 10.

Then a three-legged stent-graft prosthesis 200 is collapsed or folded to fit inside the first catheter 30 and pushed along it with the navigation element/guide wire 20 may running inside the main part of the stent-graft prosthesis and extending out through one of the legs 201.

The three-legged stent-graft prosthesis 200 is provided with a guiding element 10 attached inside one of the other legs, as described above. In an example a location near or to the left of the aortic arch is preferred.

Each guiding element 10 and navigation element 20 can be labelled at the end proximal end for easy identification. The proximally labelled end is configured to be outside of the patient during implantation.

Following, when at the correct position of the target site, the stent-graft prosthesis 200 is pushed out of the catheter 30 and allowed to fully or partially expand or unfold, as discussed above. It is rotated until the legs match the main vessel and the neck branch vessels of the aorta. And as explained above this alignment can be performed in various ways.

Next, when the three legged stent-graft prosthesis 200 is in place, the system 100 can easily be built up with further modules. As discussed above this can be done in several ways and in this example two stent-graft prostheses 1 having side branches 3 and stent-graft prostheses 600 for extending into the branch vessel are deployed following the three-legged stent-graft prosthesis 200 as described above with reference to FIGS. 1 and 2.

In the example illustrated in FIGS. 1 and 2 an extension stent-graft prosthesis 600 is navigated via the guiding element 10 attached inside one of the legs of the three-legged stent-graft prosthesis 200 and navigated through the three-legged stent-graft prosthesis 200 and positioned so that it can extend out through the leg. Here the stent-graft prosthesis 200 is expanded and connected to the leg in an overlapping manner.

Following, the first stent-graft prosthesis 300 with the side branch 3 is slid into place along the guiding element 10 and connected to the third leg 203. After or before the deployment along the guiding element 10 the second stent-graft prosthesis 300 is slid along the guidewire 20 and connected to the second leg 202.

No aortic clamping stopping blood flow in the aorta or cardioplegia is necessary. Blood flow through the aorta and the side vessels is not interrupted during the procedure thanks to the parallel arrangement of the stent-graft prostheses 300.

When delivering a stent-graft prosthesis the side branch(es) 3 are at the same time navigated into place with the stent-graft prosthesis and expanded into, or at least towards the branch vessel. Following, any additional extension stent-graft prosthesis can be inserted based on the desired need to further extend into the branch vessel.

Next, a stent-graft prosthesis 400 with two legs is moved in a collapsed state inside the first catheter 30 along guide wire 20 and guiding element 10. The stent-graft prosthesis 400 is oriented so that the legs are positioned towards the stent-graft prostheses 300 already connected. Each leg is guided along one of the guiding element 10 and the guide wire 20, so that each leg can be guided to one of the previous stent-graft prostheses 300 with side branches 3. When in place, the stent-graft prosthesis 1 is released from the catheter 30 and allowed to expand.

Alternatively, the collecting stent-graft prosthesis 400 may be connected to the proximal end of the branched stent-graft prosthesis 300 prior to connecting the side branch and/or delivering an extension stent-graft prosthesis 600.

Next a tubular shaped stent-graft prosthesis 410, without legs or side branches, is pushed into place through the catheter 30, and navigated and connected to the previous stent-graft prosthesis 400 in a similar manner but now having both the guiding element 10 and the guide wire 20 running inside. Length of the assembled prosthesis is adjustable by a variable overlap of the stent-graft prostheses chosen by the surgeon during implantation when the interconnection of these is made.

Then a two-legged stent-graft prosthesis 420 is connected to the tubular shaped stent-graft prosthesis 1 in the same manner. This two-legged stent-graft prosthesis 420 is oriented with the legs away from the stent-graft prostheses already distally connected upstream the aorta. These legs run along the guiding element 10 and the guide wire 20, respectively. The length of the assembled prosthesis is adjustable by a variable overlap of the stent-graft prostheses chosen by the surgeon during implantation when the interconnection of these is made.

After connection of the two-legged stent-graft prosthesis 420, a stent-graft prosthesis 310 with two side branches 3 is guided along the guiding element 10 through a delivery catheter, in a manner similar to previously delivered stent-graft prostheses 300. When the main body of the stent-graft prosthesis is in approximately the right place, further navigation of the side branch 3 is done to be rotationally correctly oriented towards the side vessels. The side branches 3 are thus aligned with the branch vessels and expanded into the branch vessels. Distally, the stent-graft prosthesis 310 is connected with one of the legs of the two-legged stent-graft prosthesis 420.

Then, a stent-graft prosthesis 320 with two side branches 3, and further guiding 10 or navigation elements 20, is guided via the catheter 30, aligned with branch vessels and connected to the second leg of the two-legged stent-graft prosthesis 420.

Finally, a last two-legged stent-graft prosthesis 430 is positioned and the two legs are connected to the two stent-graft prostheses 310, 320 with two side branches 3, in a similar manner as described above, by use of a delivery catheter 30 and running along the guiding element 10 and the guide wire 20, respectively.

When the system 100 is connected and complete, all remaining navigation elements 20 and catheters 30 are removed from the patient. Guiding elements 10 may be distally cut and remaining length left in place, preferably for subsequent biodegradation.

In an example, illustrated in FIG. 10, a complete system 100 is shown assembled and implanted inside an aortic arch of a patient. As can be seen, the different stent-graft prostheses 1 have been connected to each other and side branches 3 have been extended into branch vessels and further extended with stent-graft prostheses 1.

Further proximal stent-graft prosthesis modules (not shown), e.g. for iliac artery reconstruction or repair, may be provided and implanted, such as connected to the proximal end of the stent-graft prosthesis 430.

Further examples of methods and procedures are given below:

A method is provided for navigating a stent-graft prosthesis to a branch vessel. The method includes providing a stent-graft prosthesis 200, 300, 310, 320 and navigating the lateral side branch into or towards a branch vessel by moving the lateral side branch using a guiding element 10. The method may include expanding a stent-graft prosthesis delivered through the lateral side branch 3 from a collapsed state into the branch vessel when navigated in position at the branch vessel. The method may include interconnecting an expansion element 600 at the lateral side branch and into the branch vessel for further extension into the branch vessel, wherein the expansion element preferably is a stent-graft prosthesis.

A method is provided for interconnecting a plurality of stent-graft prostheses. The method includes providing a stent-graft prosthesis having a bendable guiding element connected at an exit of a side branch. The method may include interconnecting a plurality of such stent-graft prostheses including sliding a catheter by means of a guiding mate 9 along the guiding element to the exit of the side branch and delivering another stent-graft prosthesis through the catheter along the bendable guiding element for interconnection of stent-graft prostheses. The stent-graft prostheses preferably have a same dimension at the interconnection.

A medical procedure is provided including accessing 710 a target site being a vessel in a patient; delivering 720 a first stent-graft prosthesis to the inside of the vessel at the target site through a delivery catheter, wherein the target site has a side branch vessel; delivering 730 a second stent-graft prosthesis to the first stent-graft prosthesis; connecting 740 the first stent-graft prosthesis to the second stent-graft prosthesis for providing a blood flow to the side branch vessel, wherein the delivery of the second stent-graft prosthesis includes sliding a catheter along a guiding element 10 to a position inside a lumen of a side branch of the first stent-graft prosthesis; and expanding the second stent-graft prosthesis for connecting to the first stent-graft prosthesis.

A medical procedure is provided including accessing 810 a target site being a vessel in a patient; delivering 820 a first stent-graft prosthesis to the inside of the vessel at the target site through a delivery catheter, wherein the target site has a side branch vessel; expanding 830 the side branch 3; delivering 840 a second stent-graft prosthesis to the first stent-graft prosthesis and through the side branch 3 to the side vessel; and connecting 850 the first stent-graft prosthesis to the second stent-graft prosthesis for providing a blood flow to the side branch vessel.

Another example of a delivery procedure is as follows:

1. Inserting a delivery system via an introducer sheath into a patient's body.
2. Opening an outer sheath 9 and removing from a proximal end of a prosthesis towards a side branch prosthesis direction. Keep opening till the side branch prosthesis is released and expanded fully.
3. Stopping opening till the side branch prosthesis is fully exposed.
4. Adjusting the position of the prosthesis for initial matching.
5. Inserting a double lumen catheter 30 over a pre-loaded guiding element 10 and allow it travel to the side branch prosthesis, till it hits the end at connection point 11.
6. Insert an additional guidewire via the double lumen catheter 30 and make it protrude from the side branch 3.
7. Optionally performing further adjustment of the position of the prosthesis.
8. Once the position of the side vessel is identified and confirmed, advance the additional guidewire forward to secure the position.
9. Once the additional guidewire is securely staying in the side vessel, remove the double lumen catheter and deliver the connecting prosthesis 600 by using the additional guidewire and guiding element 10 over orifice element 610 for desired overlap.
10. Once the connecting prosthesis 600 is in side vessel and fully expanded, remove the rest of the outer sheath 9 of the previous prosthesis releasing it entirely.
11. Unlock the guiding element 10 from the side branch prosthesis and remove all guidewires and delivery system from the patient's body.

The present disclosure has been described above with reference to specific examples. However, other examples than the above described are equally possible within the scope of the disclosure. Different method steps than those described above, may be provided within the scope of the disclosure. The different features and steps of the disclosure may be combined in other combinations than those described. The scope of the disclosure is only limited by the appended patent claims.

What is claimed is:

1. A stent system comprising a main stent-graft prosthesis having at least one side lateral branch, said side lateral branch having a distal orifice, wherein said at least one side lateral branch comprises a connection point positioned proximally of said distal orifice of said side lateral branch, said connection point being arranged to releasably attach a distal end of a guiding element, comprising a further stent-graft prosthesis, the further stent graft prosthesis having an orifice element for receiving the guiding element there through, wherein the orifice element is an aperture in a wall structure of the further stent graft prosthesis.

2. The stent system of claim 1, wherein the connection point is arranged at an interior of said side lateral branch.

3. The stent system of claim 1, wherein the orifice element is located at a proximal portion of the further stent graft prosthesis.

4. The stent system of claim 1, wherein the side lateral branch of the main stent-graft prosthesis has a tubular wall structure.

5. The stent system of claim 1, wherein said guiding element is a textile thread or suture thread, with a radiopaque marker, such as a fiducial marker and/or a radiopaque elongate marker extending at least along a portion of a length of said guiding element.

6. The stent system of claim 1, wherein the guiding element is made of a biodegradable material.

7. A stent system comprising a main stent-graft prosthesis having at least one side lateral branch, said side lateral branch having a distal orifice, wherein said at least one side lateral branch comprises a connection point positioned proximally of said distal orifice of said side lateral branch, said connection point being arranged to releasably attach a distal end of a guiding element, comprising a further stent-graft prosthesis, the further stent graft prosthesis having an orifice element for receiving the guiding element there through, wherein the orifice element is an eyelet in a wall material of the further stent graft prosthesis.

8. A stent system comprising a main stent-graft prosthesis having at least one side lateral branch, said side lateral branch having a distal orifice, wherein said at least one side lateral branch comprises a connection point positioned proximally of said distal orifice of said side lateral branch, said connection point being arranged to releasably attach a distal end of a guiding element, wherein the side lateral branch of the main stent-graft prosthesis has a tubular wall structure, comprising a further stent-graft prosthesis having a tubular wall structure, the further stent graft prosthesis having an orifice element for receiving the guiding element there through, wherein the orifice element is an aperture in the tubular wall structure of the further stent graft prosthesis, or wherein the orifice element is an eyelet in the tubular wall structure of the further stent graft prosthesis.

* * * * *